United States Patent
Singh et al.

(12)

(10) Patent No.: US 6,365,625 B1
(45) Date of Patent: *Apr. 2, 2002

(54) COMPOUND FOR INHIBITING HIV INFECTIVITY

(75) Inventors: Shyam K. Singh, Arlington; Raymond J. Patch, Framingham; Peter V. Pallai, Westwood; Edith A. Neidhardt, Boxford; Gerard P. Palace, Framingham; Kevin J. Willis, Newton; Theresa M. Sampo, Watertown, all of MA (US); Kevin W. McDonald, Merrimack, NH (US); Zhan Shi, Waltham, MA (US)

(73) Assignee: Procept, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/398,571

(22) Filed: Sep. 17, 1999

Related U.S. Application Data

(63) Continuation of application No. 08/467,728, filed on Jun. 6, 1995, now Pat. No. 6,075,050, which is a continuation-in-part of application No. 08/245,619, filed on May 19, 1994, now Pat. No. 5,614,559, which is a continuation-in-part of application No. 08/156,443, filed on Nov. 23, 1993, now abandoned.

(51) Int. Cl.$^7$ .................... A61K 31/185; C07C 309/35; C07C 309/32
(52) U.S. Cl. ................... 514/517; 514/518; 514/576; 514/577; 514/764; 514/765; 558/45; 558/46; 562/88; 562/89; 562/429
(58) Field of Search ................... 514/517, 518, 514/576, 577, 764, 765; 558/45, 46; 562/88, 89, 429

(56) References Cited

U.S. PATENT DOCUMENTS

| | | | |
|---|---|---|---|
| 4,361,547 A | 11/1982 | Sipos et al. | 424/56 |
| 4,362,712 A | 12/1982 | Buck | 424/49 |
| 4,364,927 A | 12/1982 | Sipos et al. | 424/56 |
| 4,403,089 A | 9/1983 | Buck | 528/247 |
| 4,590,070 A | 5/1986 | Chantler et al. | 424/78 |
| 4,604,404 A | 8/1986 | Munson, Jr. et al. | 514/494 |
| 5,028,736 A | 7/1991 | Girrbach et al. | 562/89 |
| 5,177,083 A | 1/1993 | Rideout et al. | 514/296 |
| 5,308,612 A | 5/1994 | Lee | 424/78.35 |
| 5,312,837 A | 5/1994 | Hwang et al. | 514/577 |
| 5,424,063 A | 6/1995 | Cardin et al. | 424/78.08 |
| 5,614,559 A | 3/1997 | Singh et al. | 514/577 |
| 6,075,050 A | * 6/2000 | Singh et al. | 514/517 |

FOREIGN PATENT DOCUMENTS

| | | |
|---|---|---|
| EP | 0 099 477 | 6/1983 |
| EP | 0 384 532 | 8/1990 |
| FR | 2 669 535 | 5/1992 |
| WO | WO 92/12709 | 8/1992 |
| WO | WO 93/14146 | 7/1993 |
| WO | WO 94/03164 | 2/1994 |
| WO | WO 94/14763 | 7/1994 |
| WO | WO 95/14479 | 6/1995 |
| WO | WO 96/28169 | 9/1996 |

OTHER PUBLICATIONS

Taylor, D. L., et al., "Novel Sulphonic Acid Polymers as Inhibitors of HIV Host–Cell Interactions," Abstract PO–B26–2071, *IXth International Conference on Aids*, Jun. 6–11, 1993.

Tan, Ghee T., et al., "Sulfonic acid polymers are potent inhibitors of HIV–1 induced cytopathogenicity and the reverse transcriptases of both HIV–1 and HIV–2," *Biochimica et Biophysica Acta*, 1181:183–188 (1993).

Mohan, Prem, et al., "Sulfonic acid polymers as a new class of human immunodeficiency virus inhibitors," *Antiviral Research*, 18:139–150 (1992).

Rusconi, S. et al., "In Vitro Inhibition of HIV–1 by a New Class of CD4–Binding Drugs," Abstract from the *IXth International Conference on AIDS*, 1993 (Abstract No.: WS–A17–1).

Kozlowski, et al., *Antiviral Chemistry & Chemotherapy* 3(1), 49–53 (1992).

Aldrich Catalog, Aldrich Chemical Co., #20,205–3 (Compound 6537–6627) p. 561 (1990).

Douves et al., *Proc. Natl. Acad. Sci.*, vol. 88:6328–6332 (1991).

Norkin, et al., *Clinical Microbiology Reviews*, 995:193–315 (1995).

* cited by examiner

*Primary Examiner*—Peter O'Sullivan
(74) *Attorney, Agent, or Firm*—Hamilton, Brook, Smith & Reynolds P.C.

(57) ABSTRACT

This invention pertains to the discovery that condensation polymers of an aldehyde and aromatic sulfonic acids and fractions thereof, such as formaldehyde naphthalenesulfonic acid condensation polymers, can abrogate HIV gp120 binding to CD4, as demonstrated in CD4/gp120 binding assays. In addition to gp120 binding inhibition, the compounds have been shown to inhibit HIV-induced syncytia formation and infectivity of CD+ cells. The use of this compound has been shown to be non-cytotoxic and non-inhibitory to antigen induced T lymphocyte proliferation. Based on these findings, these compounds can be used as a therapeutic agent for the treatment of acquired immunodeficiency syndrome (AIDS), as well as AIDS-related complex (ARC), AIDS-related dementia and non-symptomatic HIV infection. The compounds can also be used to treat blood preparations.

6 Claims, 18 Drawing Sheets

COMPOUND FOR INHIBITING HIV INFECTIVITY

RELATED APPLICATION

This application is a continuation of U.S. application Ser. No. 08/467,728, filed on Jun. 6, 1995, now U.S. Pat. No. 6,075,050 which is a continuation-in-part of U.S. application Ser. No. 08/245,619 filed May 19, 1994, U.S. Pat. No. 5,614,559, which is a continuation-in-part of U.S. application Ser. No. 08/156,443 filed Nov. 23, 1993, now abandoned, the teachings of which are incorporated by reference herein in their entirety.

BACKGROUND OF THE INVENTION

CD4, a surface glycoprotein receptor found on a subset of T lymphocytes known as CD4+ cells, is involved in Class II major histocompatibility complex (MHC) recognition and appears to be the physiological receptor for Class II MHC. Human CD4 is also the receptor for the gp120 envelope glycoprotein of the human immunodeficiency virus (HIV) and is essential for virus entry into the host cell, and for membrane fusion, both of which contribute to cell-to-cell transmission of the virus and to its cytopathic effects. It is known that HIV causes AIDS by attacking the immune system and destroying CD4+ cells, thus leaving the body defenseless against attack by microbial and other viral pathogens. CD4 has been shown to be the major route of entry of HIV into CD4+ cells by binding to CD4.

Considerable effort has been expended in studying the CD4gp120 interaction and in trying to interfere with or inhibit that interaction, in an attempt to provide a means by which the life threatening effects of HIV infection can be slowed or reversed. Thus far, a small number of anti-viral drugs have been developed to interfere with infection of cells by HIV and its subsequent effects, such as zidovudine (also known as AZT) or dideoxyinosine (ddI). A means by which to prevent HIV infection of CD4-bearing lymphocytes, which make up approximately 60–80% of the total circulating T lymphocyte population, would be of great value, particularly in light of the fact that HIV infection of such cells can cause total collapse of the immune system and would be expected to avoid development of a viral resistance to the therapy. One compound, dextran-sulfate, was thought to interfere with CD4gp120 interaction. However, the compound resulted in unacceptable levels of anti-coagulation activity. Recently, dextran sulfate reportedly failed to suppress infection by monocytotropic HIV-1 isolates (Meylan, P. R. A. et al., *Antimicrob. Agents Chemother.* 38:2910–2916 (1994)). It would be of further value to develop agents that can be used to treat CD4-related diseases such as AIDS-related complex (ARC), AIDS-related dementia and non-symptomatic HIV infection which avoid significant levels of anti-coagulation activity.

Many condensation polymers of formaldehyde and aromatic sulfonic acids have been previously described. U.S. Pat. No. 4,604,404 discloses the use of some such polymers as antiviral agents against the Herpes simplex virus. However, the reference does not teach or suggest the use of such compounds in the treatment of HIV infections and related diseases and conditions.

SUMMARY OF THE INVENTION

This invention relates to the discovery that condensation polymers of aromatic sulfonic acids and an aldehyde and fractions thereof, particularly naphthalenesulfonic acid formaldehyde polymers (such as PRO 1041, PRO 1135 and PIC 024.4, and fractions thereof defined below) can abrogate HIV gp120 binding to CD4, as demonstrated in CD4/gp120 binding assays. Compounds of the present invention have been shown to have little to no cytotoxicity and inhibitory activity to antigen induced T-lymphocyte proliferation and exhibit specificity as manifested by lack of inhibition in CD2/LFA-3 (lymphocyte function-associated antigen) (CD58) binding assay. Based on these findings, condensation polymers of aromatic sulfonic acids and an aldehyde and fractions thereof can be used as therapeutic agents for the prophylaxis or treatment of HIV infection, acquired immunodeficiency syndrome (AIDS), as well as AIDS-related complex (ARC), AIDS-related dementia and non-symptomatic HIV infection. The compounds can also be used to treat a blood preparation in vitro to prevent HIV infection of CD4+ cells present in the blood preparation.

Figure 10A:
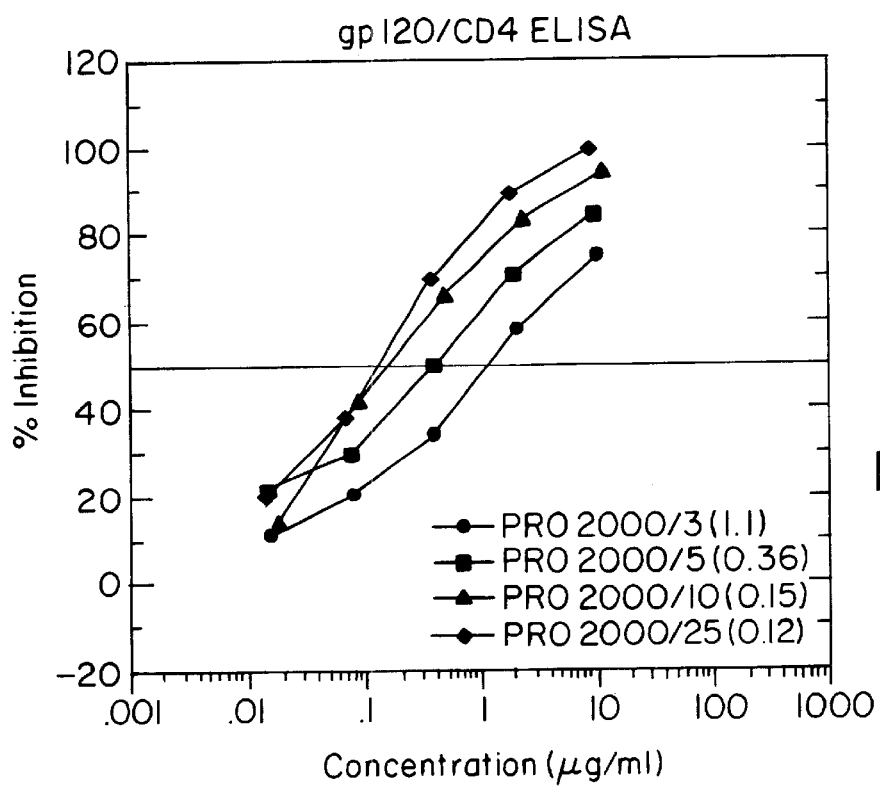
FIGS. 10A and 10B are graphic illustrations of the inhibition of gp120 binding to CD4 by ELISA for PRO 2000/3
Figure 10B:
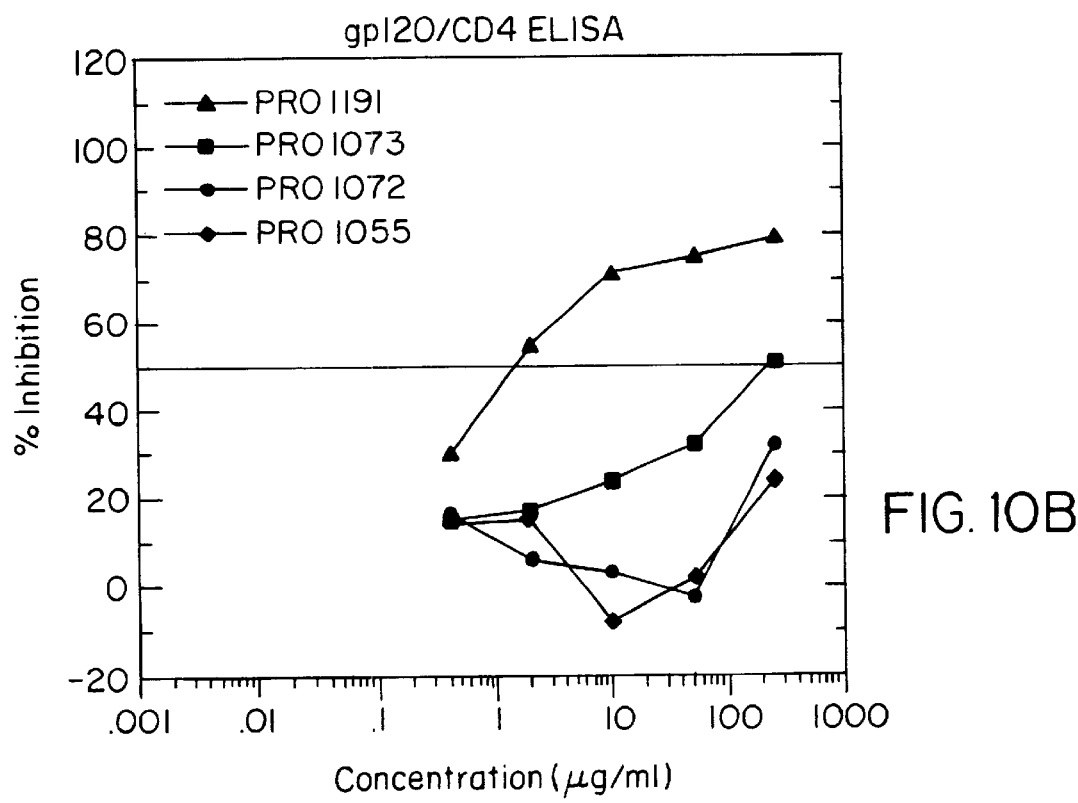

(circles), PRO 2000/5 (squares), PRO 2000/10 (triangles), PRO 2000/25 (diamonds) (FIG. 10A), PRO 1055, PRO 1072, PRO 1073 and PRO 1191 (FIG. 10B). IC$_{50}$s (in µg/ml) are parenthesized.

Figure 11:
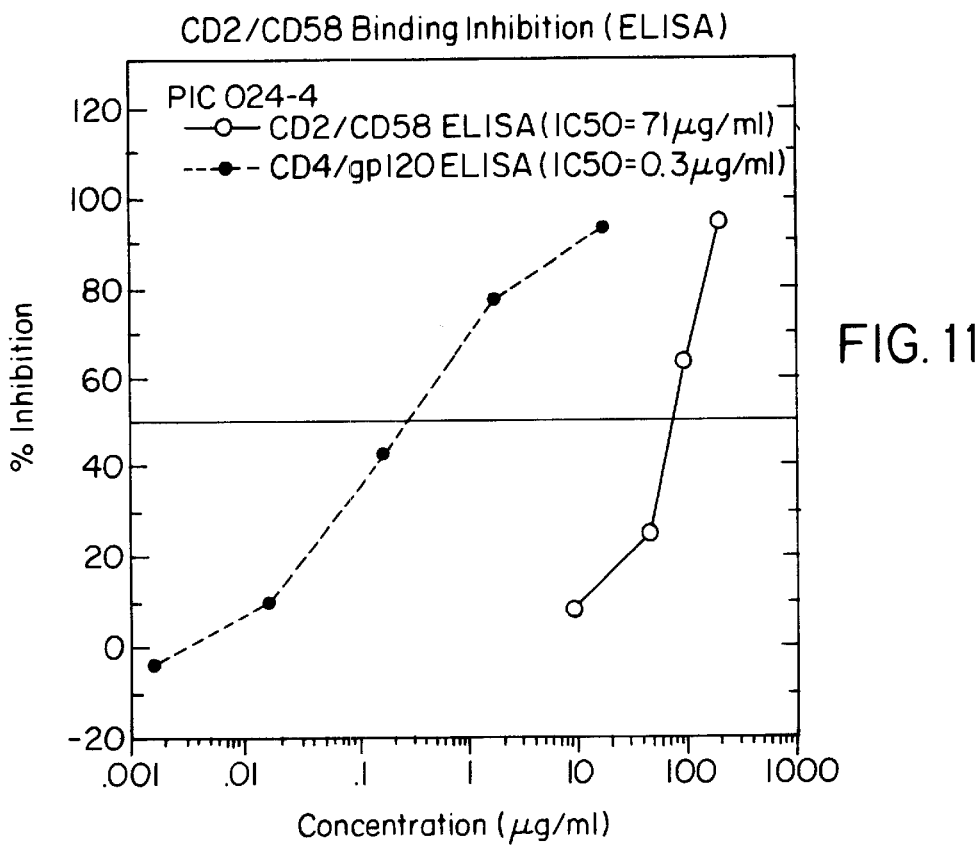

FIG. 11 is a graphic illustration of the inhibition of CD2 binding to CD58 by PIC 024.4. Curve for the inhibition of gp120 binding to CD4 is shown for comparison.

Figure 12:
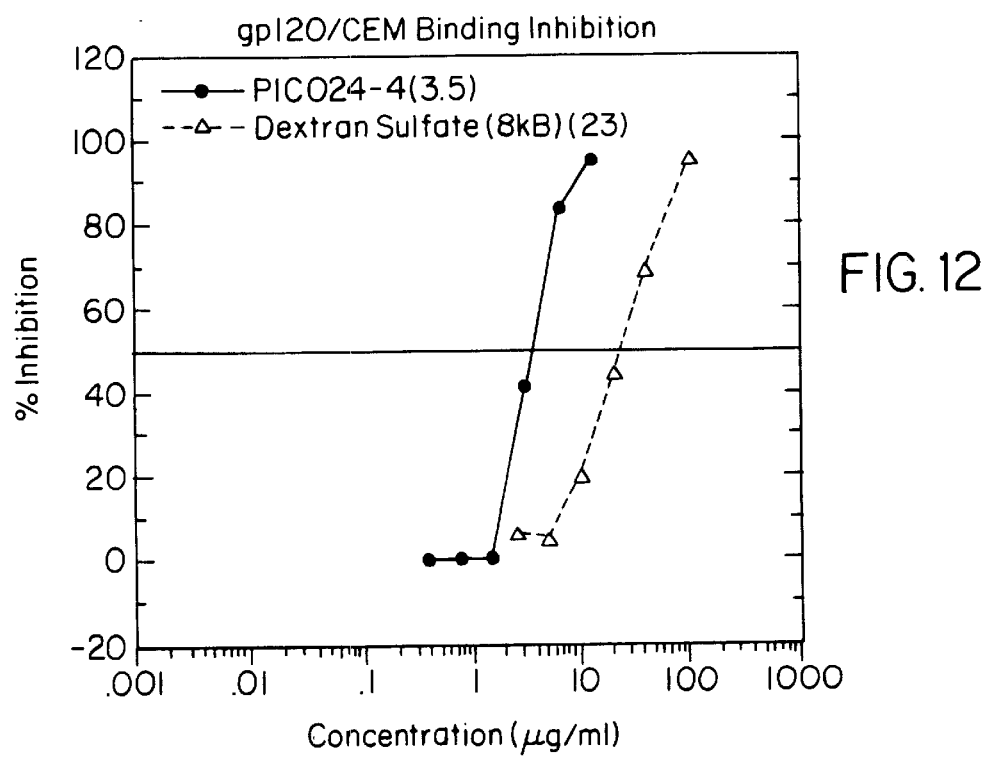

FIG. 12 is a graphic illustration of the inhibition of gp120 binding to CEM cells by PIC 024.4 (closed circles) and dextran sulfate, 8 kD (open triangles). IC$_{50}$'s (in µg/ml) are parenthesized.

Figure 13A:
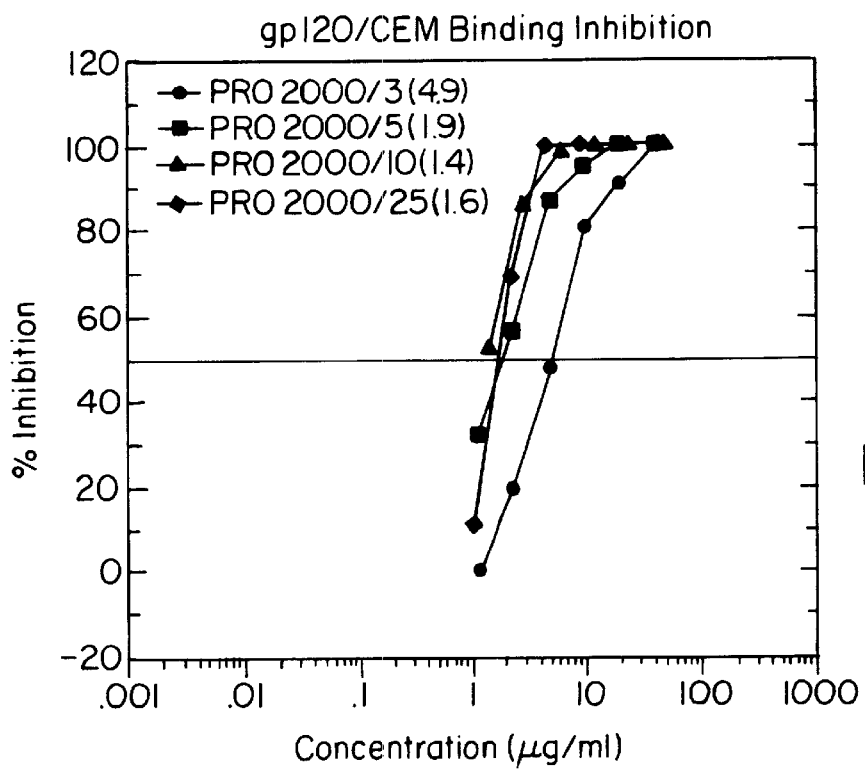
Figure 13B:
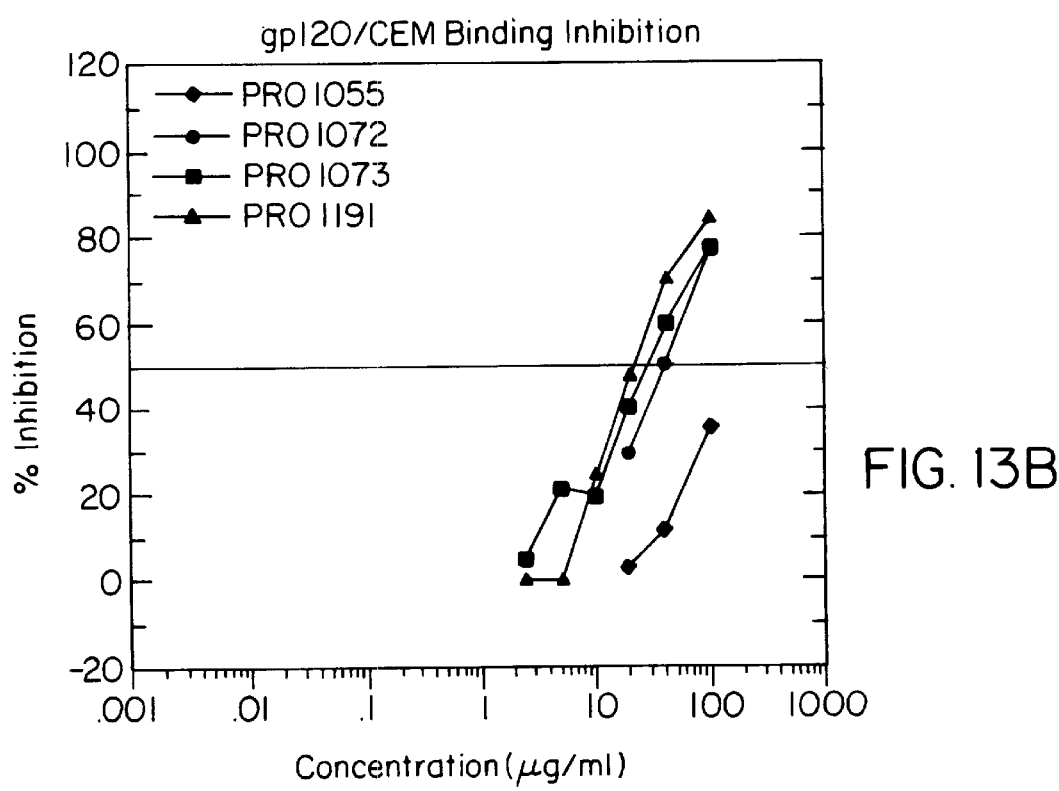

FIGS. 13A and 13B are graphic illustrations of the inhibition of gp120 binding to CEM cells by PRO 2000/3 (circles), PRO 2000/5 (squares), PRO 2000/10 (triangles), PRO 2000/25 (diamonds) (FIG. 13A) PRO 1055, PRO 1072, PRO 1073 and PRO 1191 (FIG. 13B). IC$_{50}$s (in µg/ml) are parenthesized.

Figure 14:
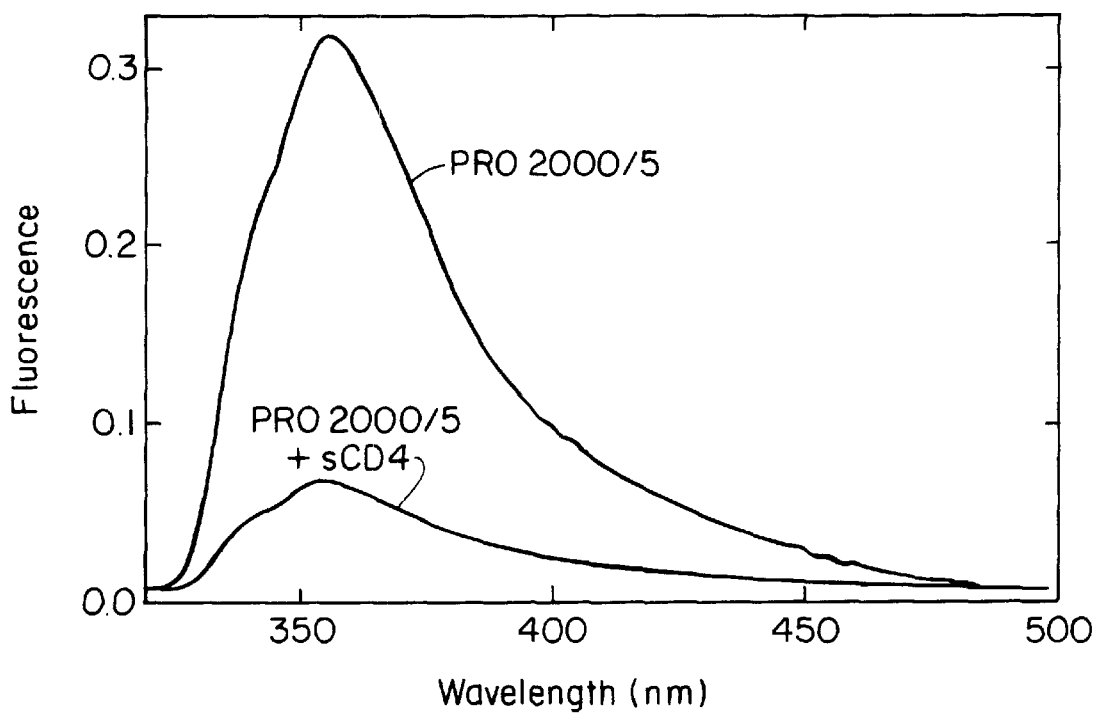
Figure 14A:
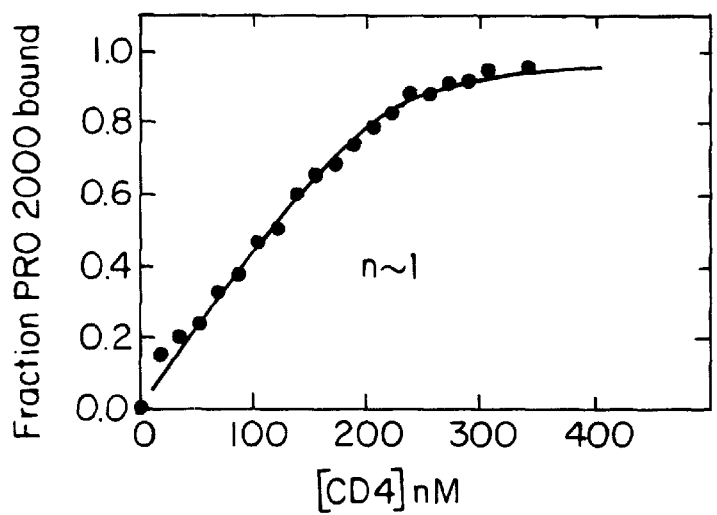

FIG. 14 and FIG. 14A are graphic illustrations of the fluorescence spectra of PRO 2000/5 in the absence and presence of recombinant, soluble CD4. FIG. 14A illustrates the fraction of polymer bound with added CD4.

Figure 15A:
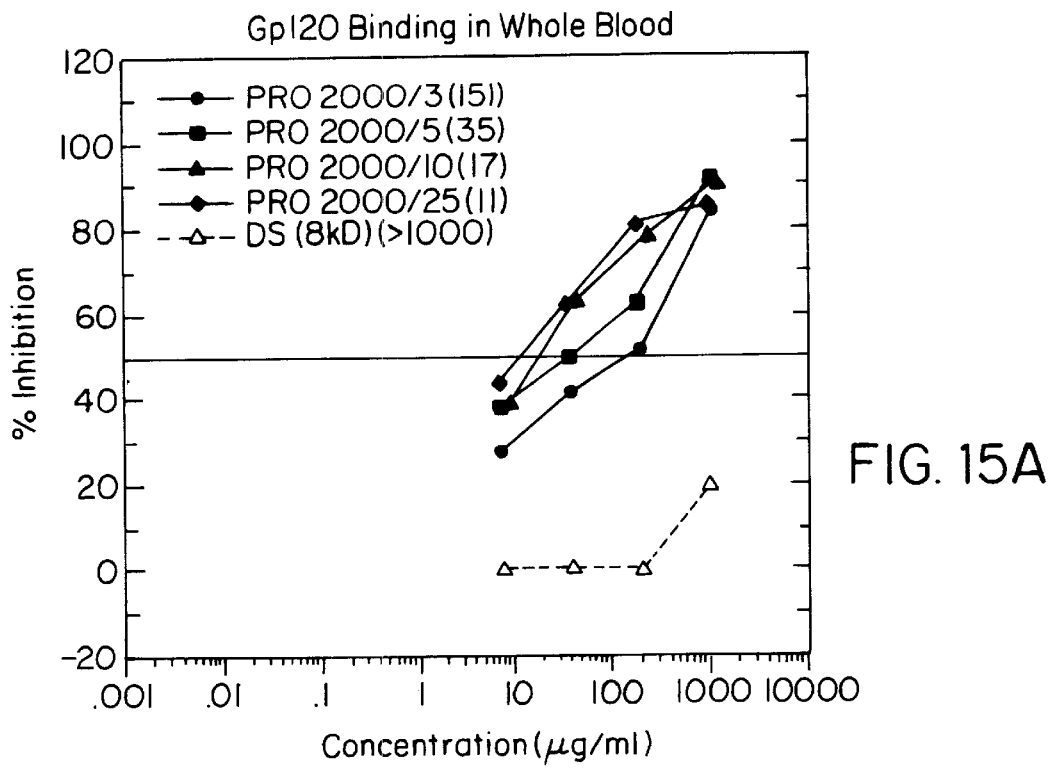
Figure 15B:
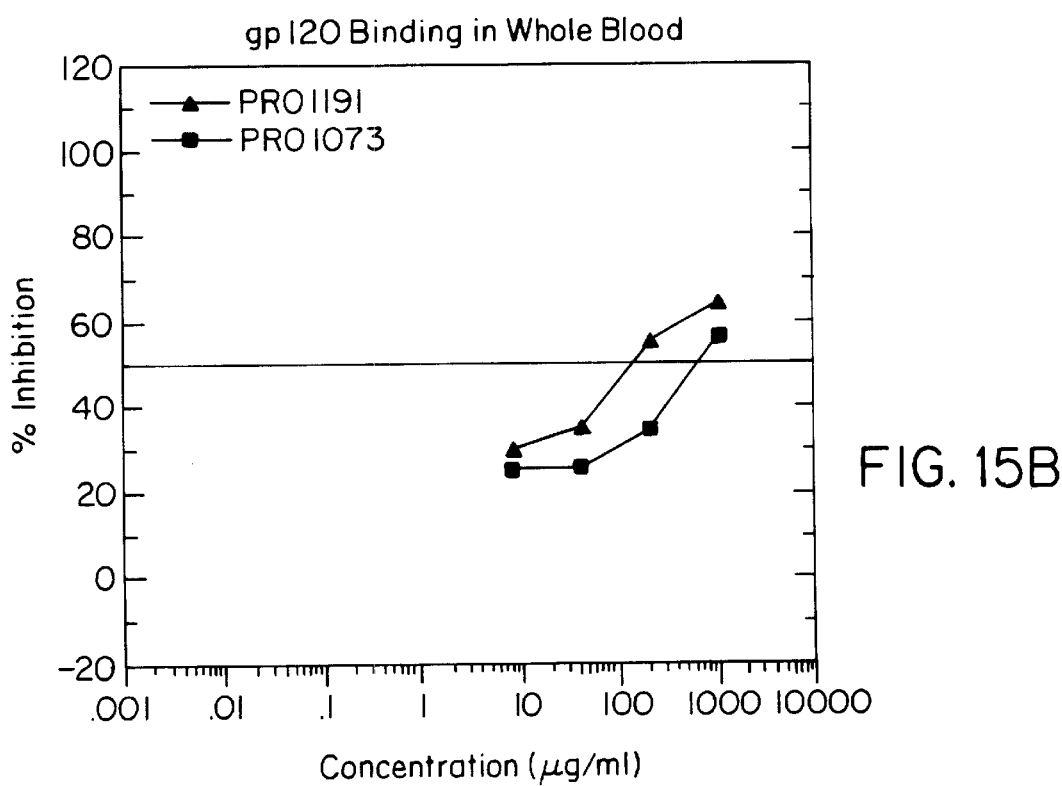

FIGS. 15A and 15B are graphic illustrations of the inhibition of gp120 binding to lymphocytes in whole blood by PRO 2000 fractions for PRO 2000/3 (circles), PRO 2000/5 (squares), PRO 2000/10 (triangles), PRO 2000/25 (diamonds) (FIG. 15A), PRO 1073 and PRO 1191 (FIG. 15B). IC$_{50}$s (in µg/ml) are parenthesized.

Figure 16:
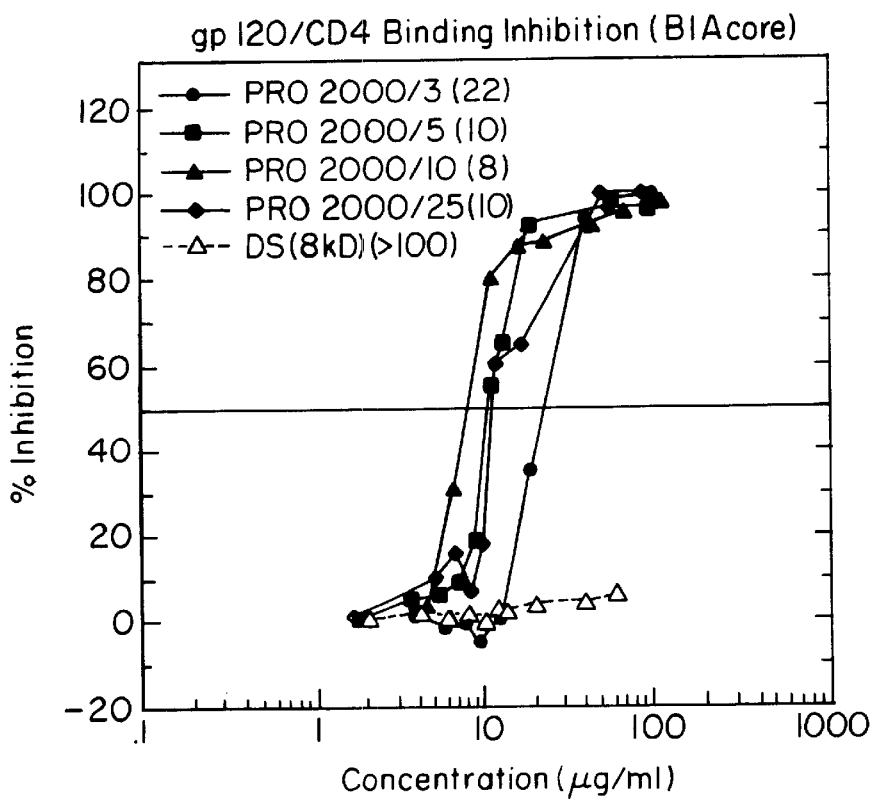

FIG. 16 is a graphic illustration of the inhibition of gp120 binding to CD4 on an surface plasma resonance (SPR)-biosensor for PRO 2000/3 (circles), PRO 2000/5 (squares), PRO 2000/10 (triangles), PRO 2000/25 (diamonds). IC$_{50}$s (in µg/ml) are parenthesized.

Figure 17A:
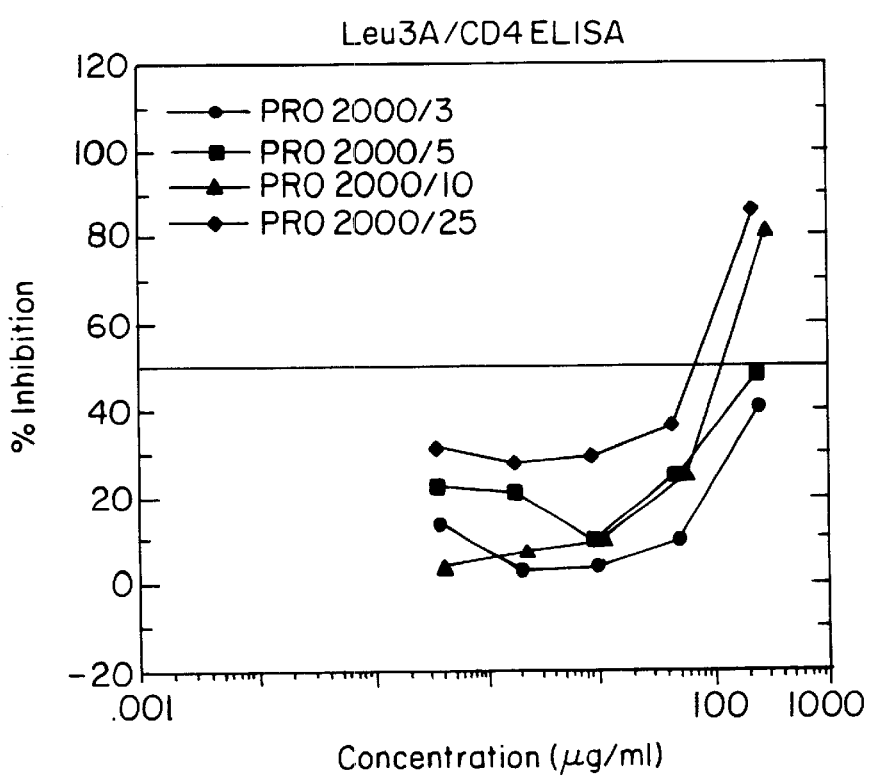
Figure 17B:
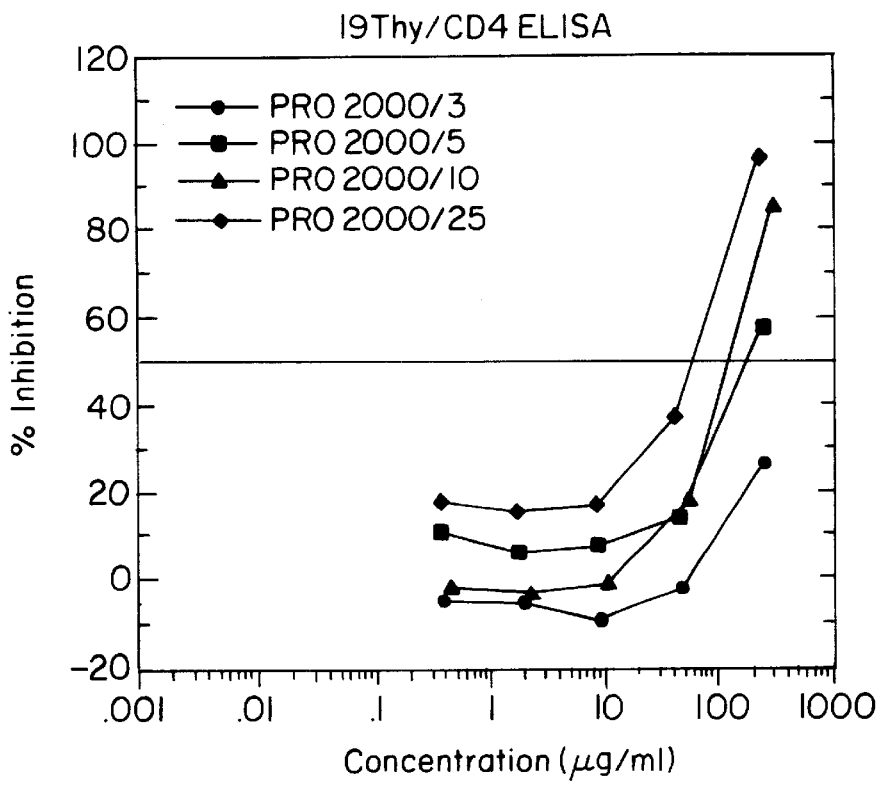
Figure 17C:
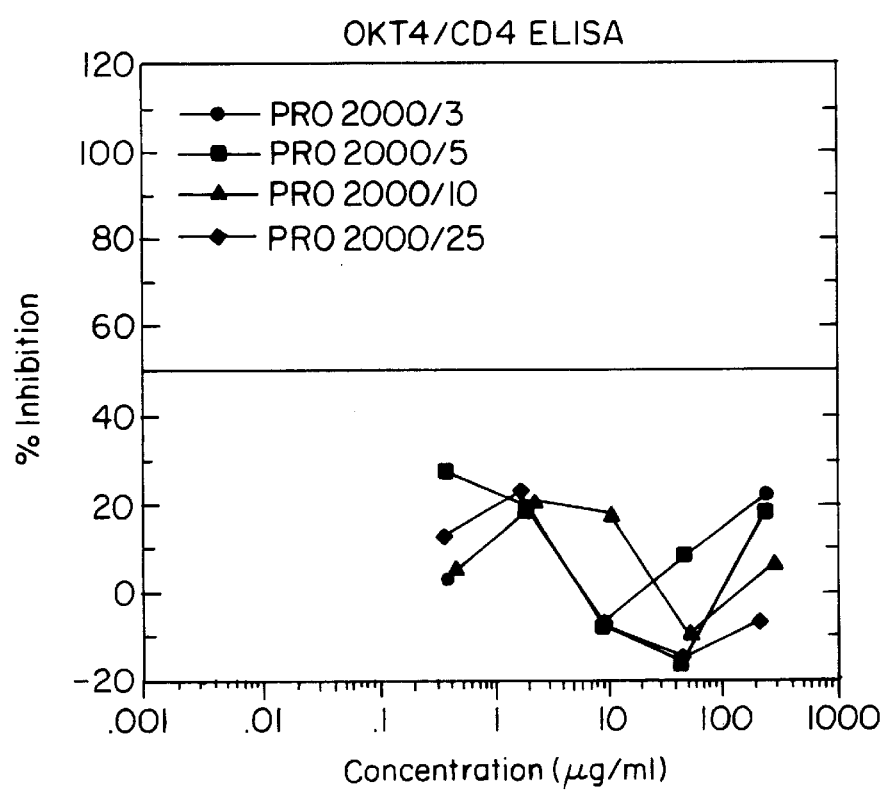

FIGS. 17A, 17B and 17C are graphic illustrations of the inhibition of monoclonal antibody binding to CD4 in ELISA. 17A: Leu3A; 17B: 19Thy; 17C: OKT4. PRO 2000/3 (circles), PRO 2000/5 (squares), PRO 2000/10 (triangles), PRO 2000/25 (diamonds).

Figure 18A:
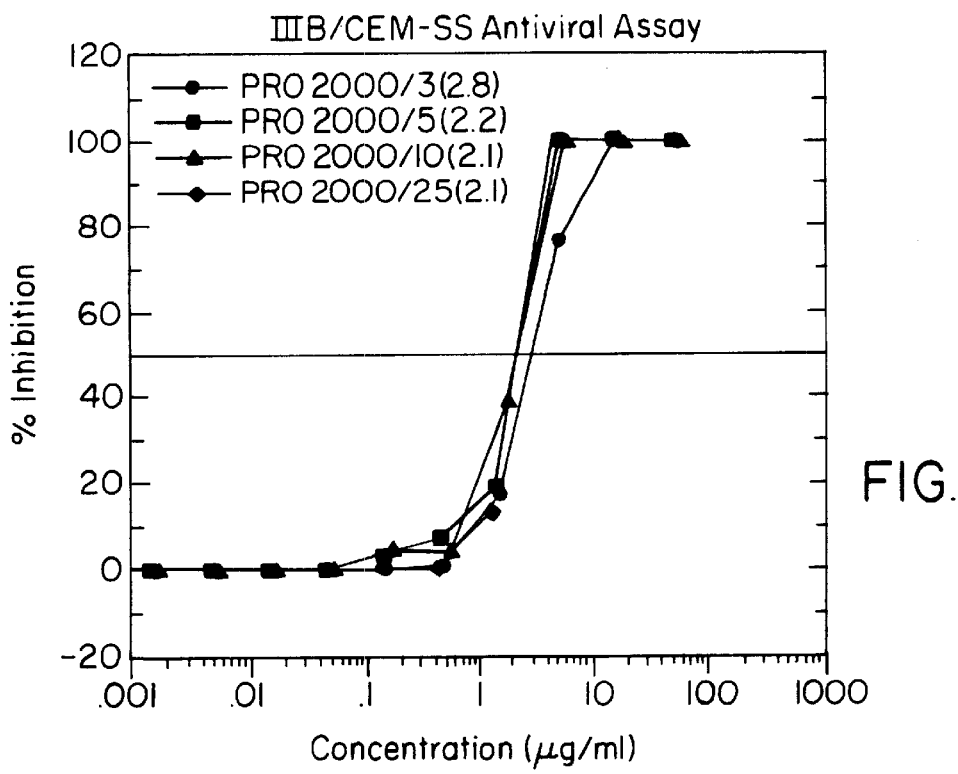
Figure 18B:
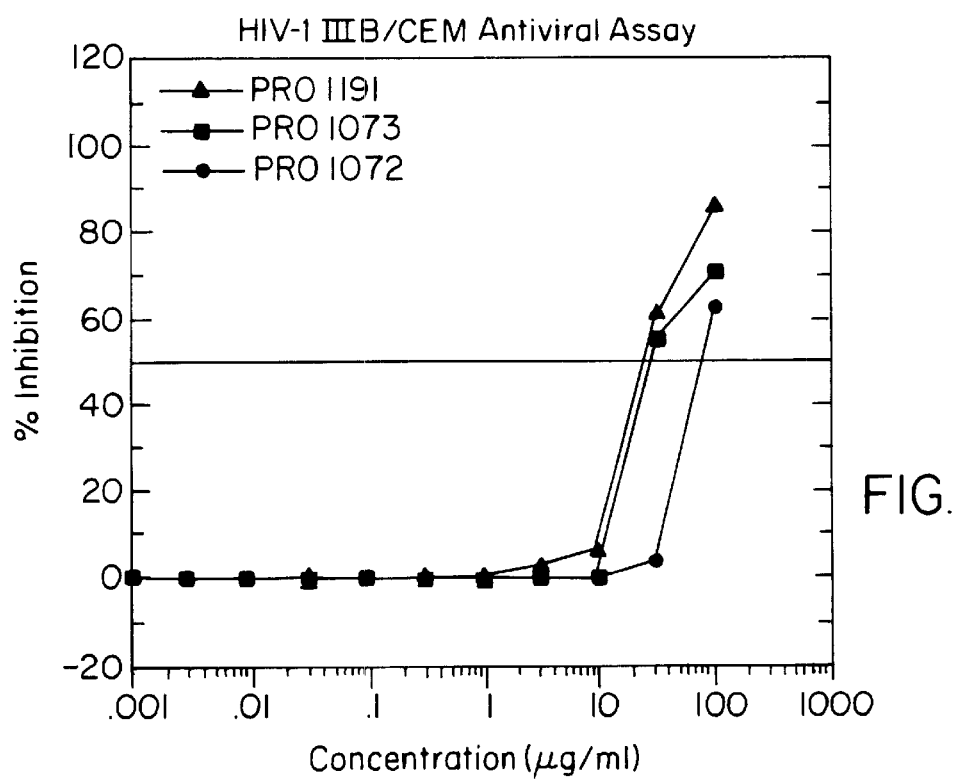

FIGS. 18A and 18B are graphic illustrations of the inhibition of HIV-1 IIIB infection of CEM-SS cells by PRO 2000 fractions; PRO 2000/3 (circles), PRO 2000/5 (squares), PRO 2000/10 (triangles), PRO 2000/25 (diamonds) (FIG. 18A, PRO 1072, PRO 1073 and PRO 1191 (FIG. 18B). IC$_{50}$s (in µg/ml) are parenthesized.

Figure 19:
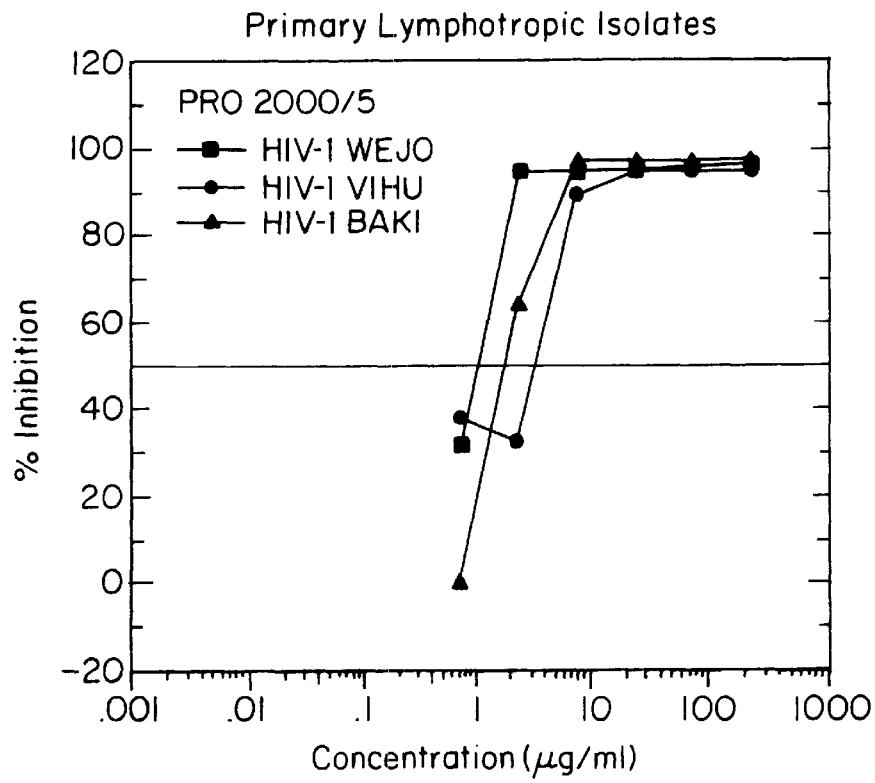

FIG. 19 is a graphic illustration of the inhibition of infection by HIV-1 primary clinical isolates by PRO 2000/5.

Figure 20:
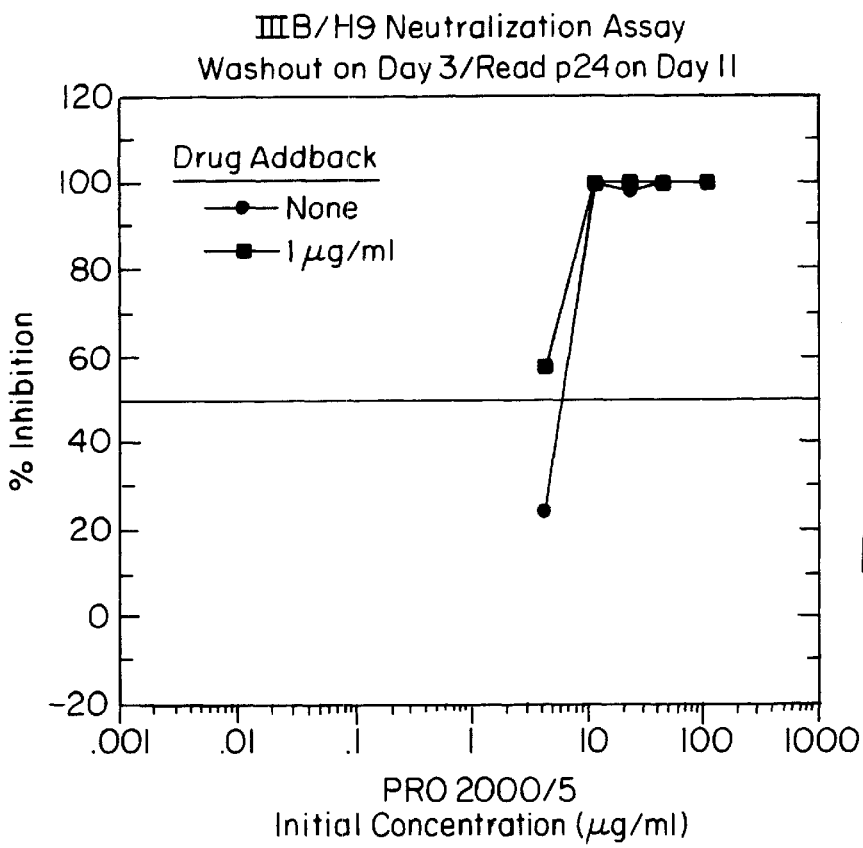

FIG. 20 is a graphic illustration of the inhibition of HIV-1 IIIB growth on H9 cells by PRO 2000/5 following drug washout on day 3. Circles: no drug added back at day 3; squares: PRO 2000/5 added back at 1 µg/ml at day 3.

Figure 21:
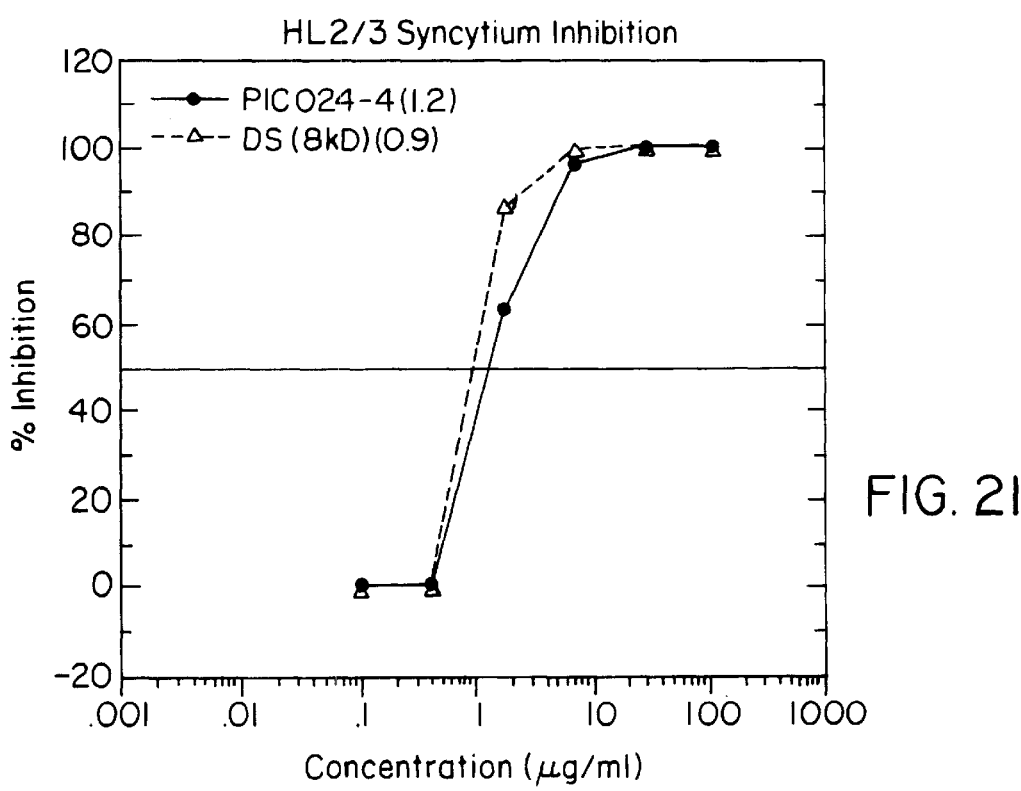

FIG. 21 is a graphic illustration of the inhibition of syncytium formation by PIC 024.4. PIC 024.4 (closed circles); dextran sulfate, 8 kD (open triangles). IC$_{50}$'s (in µg/ml) are shown in parentheses.

Figure 22A:
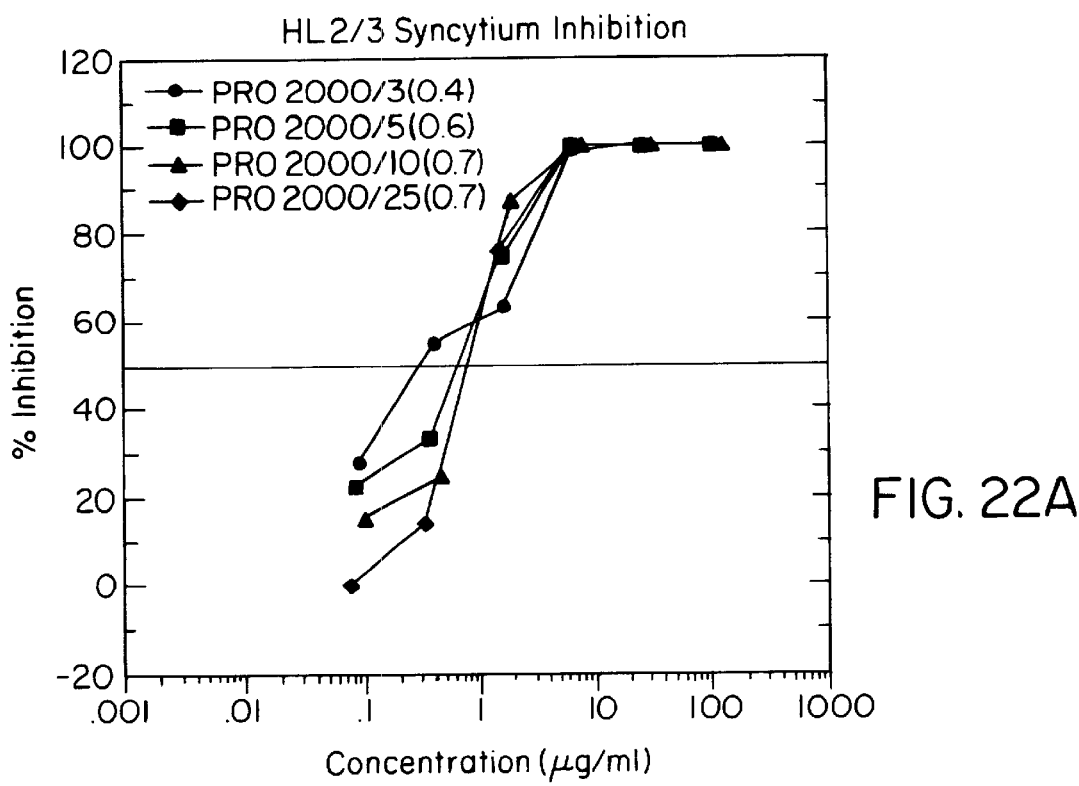
Figure 22B:
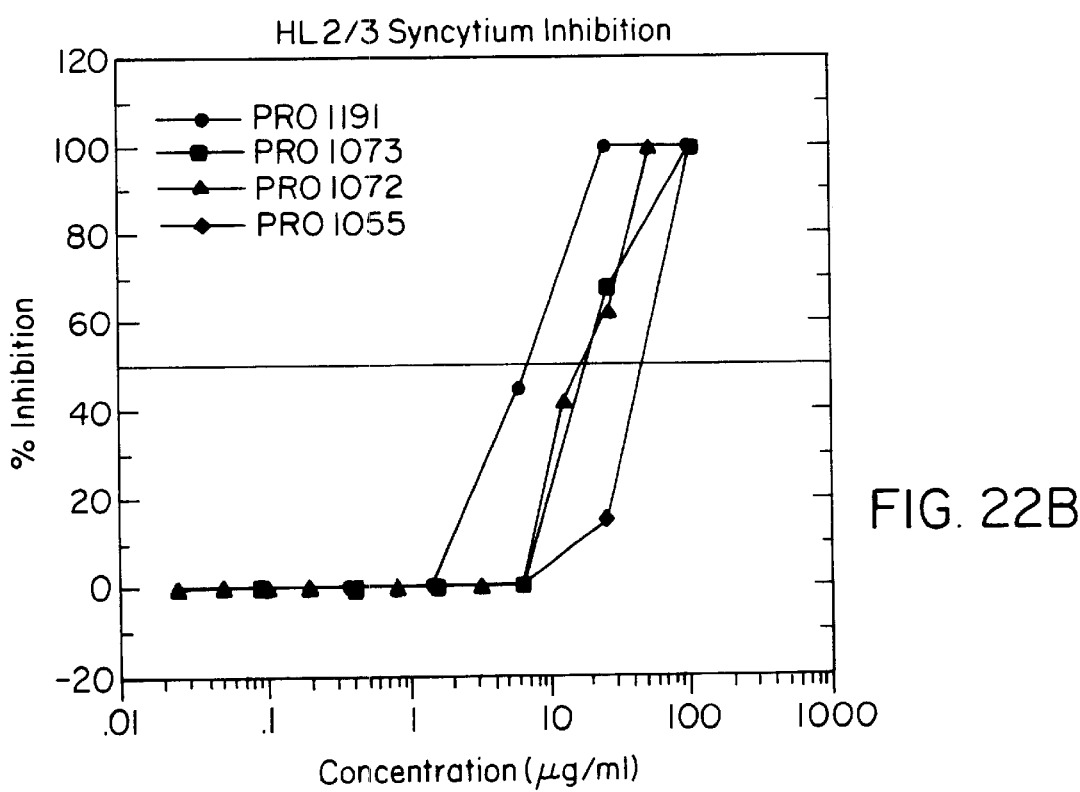

FIGS. 22A and 22B are graphic illustrations of the inhibition of syncytium formation by PRO 2000 fractions. PRO 2000/3 (circles); PRO 2000/5 (squares) PRO 2000/10 (triangles), PRO 2000/25 (diamonds) (FIG. 22A), PRO 1055, PRO 1072, PRO 1073 and PRO 1191 (FIG. 22B). IC$_{50}$'s (in µg/ml) are shown in parentheses.

Figure 23:
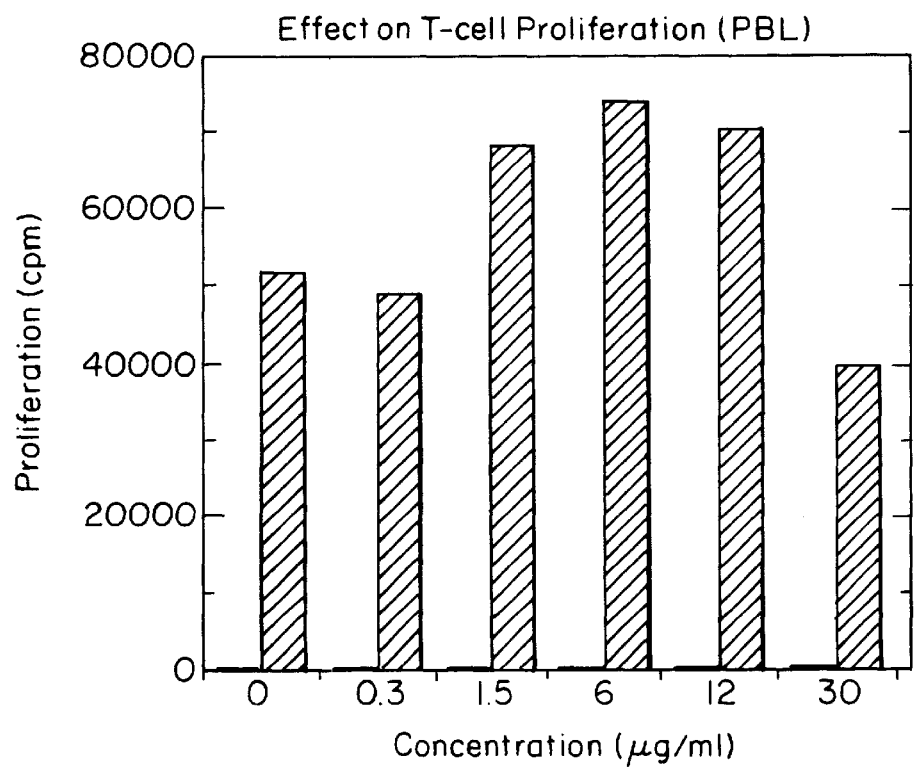

FIG. 23 is a bar graph of the effect of PIC 024.4 on antigen-dependent proliferation of human PBMCs. Effect on tetanus toxoid-dependent proliferation (hatched bars); effect on unstimulated cells (solid bars).

Figure 24:
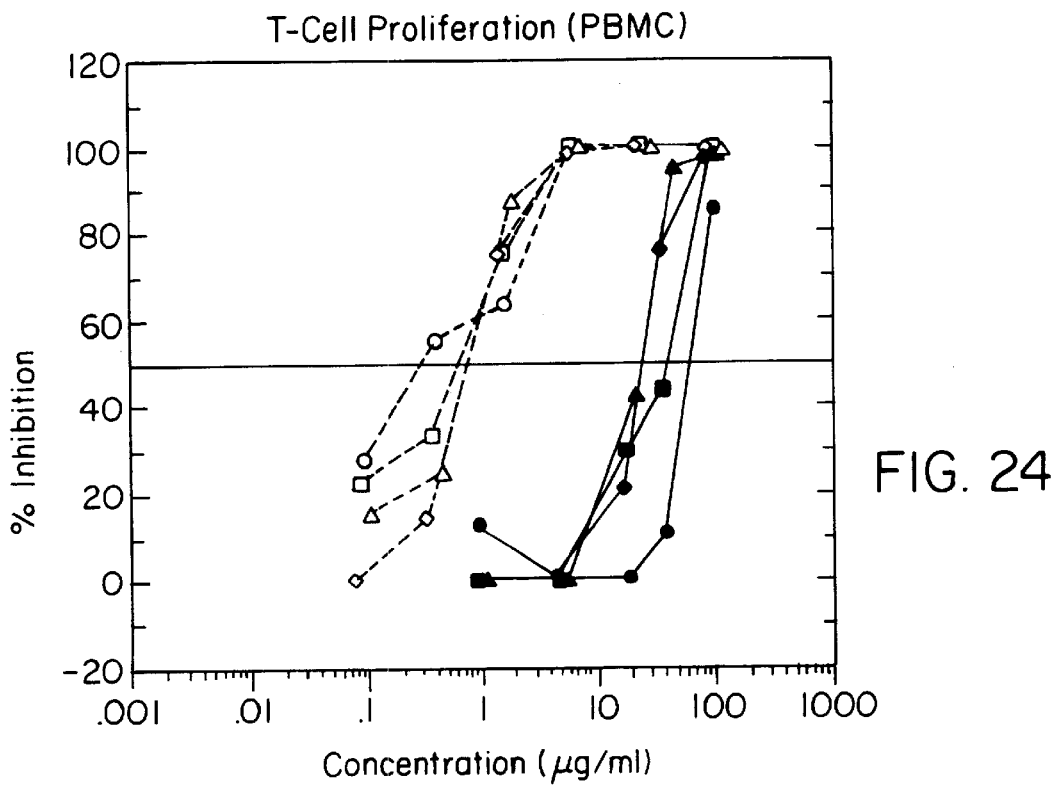

FIG. 24 is a graphic illustration of the effect of PRO 2000 fractions on normal antigen-dependent proliferation of PBMCs. Effect on lymphoproliferation (closed symbols); effect on syncytium formation (open symbols); PRO 2000/3 (circles); PRO 2000/5 (squares); PRO 2000/10 (triangles); PRO 2000/25 (diamonds).

Figure 25:
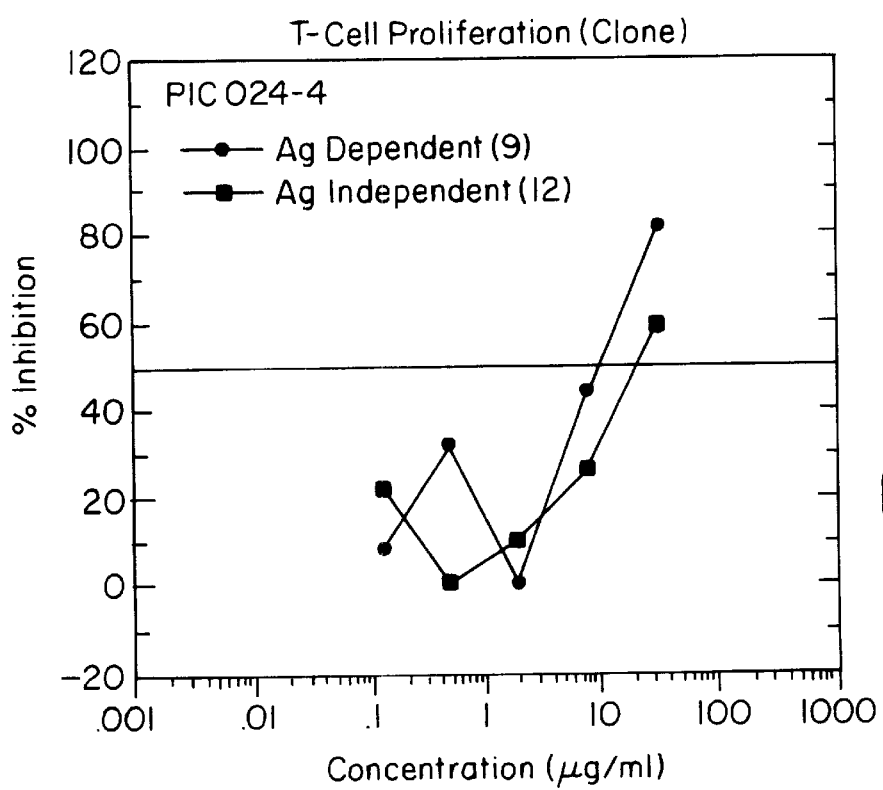

FIG. 25 is a graphic illustration of the effect of PIC 024.4 on antigen-dependent and Il-2-mediated proliferation of a T cell clone.

Figure 26A:
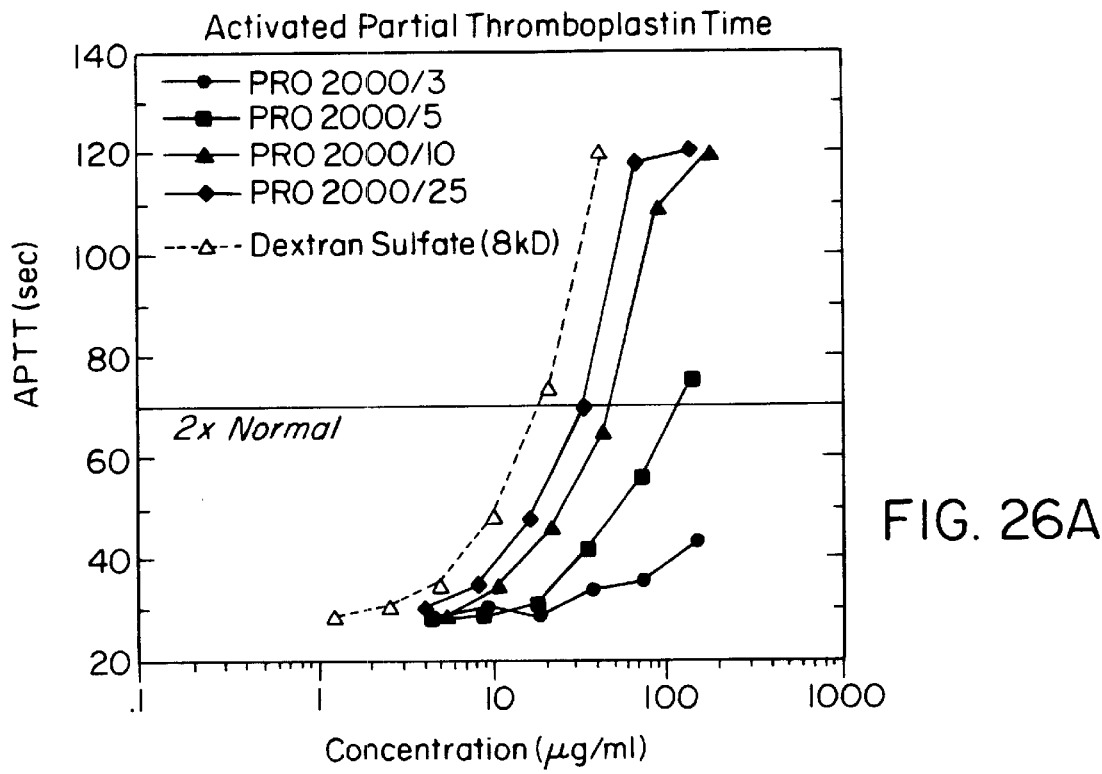
Figure 26B:
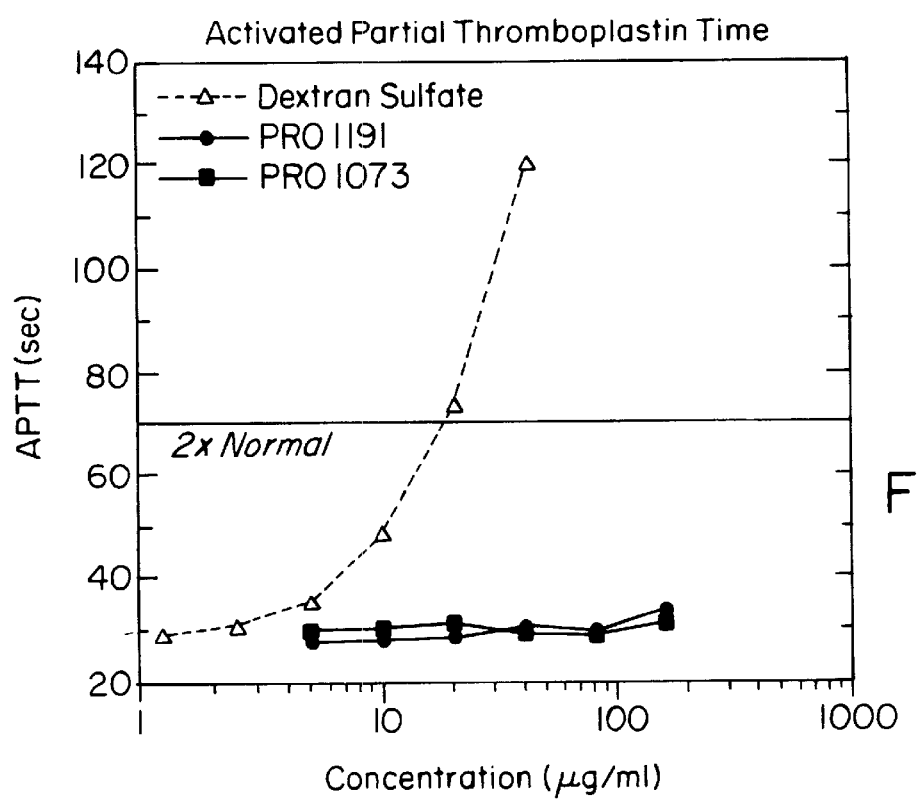

FIGS. 26A and 26B compare the Activated Partial Thrombosis Time (APTT) with each PRO 2000/3, PRO 2000/5, PRO 2000/10, PRO 2000/25 (FIG. 26A), PRO 1073, PRO 1191 (FIG. 26B), and dextran sulfate.

DETAILED DESCRIPTION OF THE INVENTION

The preparation of aldehyde condensation polymers of aromatic sulfonic acids is generally known in the art. The polymers possess the general structure:

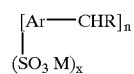

Aromatic sulfonic acids, as employed herein, include aromatic carbocyclic and heterocyclic rings substituted by one or more sulfonic acid moieties (e.g., x can be 1 to 4). Aromatic carbocyclic rings (Ar) include phenyl, naphthyl, tetrahydronaphthyl, biphenyl, phenylalkylphenyl, phenylalkenylphenyl, phenoxyphenyl, phenylthiophenyl and phenoxyalkoxyphenyl, for example. Aromatic heterocyclic rings (Ar) include, pyridinyl, pyrimidinyl, quinolinyl, thiophenyl, furanyl, pyrazolyl, imidazolyl, pyrrolyl and thiazolyl, for example. Aldehydes (CHRO) useful in the preparation of compounds for the present invention include formaldehyde, acetaldehyde, propionaldehyde and benzaldehyde, for example. Preferably, the aldehyde is formaldehyde. Correspondingly, R of the formula can be hydrogen, substituted or unsubstituted alkyl (preferably lower alkyl), substituted or unsubstituted aryl (such as, phenyl). Substituents include, for example, alkyl, alkoxy, aryl, aryloxy, halogen, hydroxy, amino, alkylamino, dialkylamino, carboxyl, sulfonate and phosphorate. The polymer can be a free acid, or a pharmaceutically acceptable salt. Alternatively, the polymer can be administered as a prodrug. Thus, M can be hydrogen, a pharmaceutically acceptable cation (e.g., an alkali metal, alkaline earth metal, or ammonium group), or a sulfonate blocking group which will preferably cleave in vivo (e.g. a linear or branched alkyl). The term "polymer", as employed herein, includes any compound formed by the coupling of two or more monomers or repeating units (e.g., n is an integer of two or more). U.S. Pat. No. 4,604,404 exemplifies suitable polymers useful herein and methods of preparing them, the teachings therein being incorporated by reference.

A particularly preferred polymer is the condensation product of a naphthalene sulfonic acid and formaldehyde of the formula:

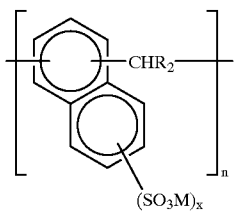

Wherein x is 1 or 2; $R_2$ is hydrogen, alkyl, alkoxy or an anionic group, such as carboxy and phosphonate; M is hydrogen, a pharmaceutically acceptable cation or a sulfonate blocking group which will cleave in vivo. It can be desirable to block a fraction or all of the sulfonic acid groups to improve bioavailability of the polymer. In some instances, it may be desirable to irreversibly block a fraction of the sulfonic acid groups.

The polymers of the present invention also include copolymers wherein the aldehyde and/or aromatic sulfonic acid are added as mixtures of different aldehydes and/or aromatic sulfonic acids (such as those defined above). Also included are copolymers wherein an aromatic group, not substituted by sulfonic acid, is added. For example, the aromatic group can be a carbocyclic or heterocyclic group (as defined above) unsubstituted or substituted by one or more groups, such as alkyl, alkoxy, aryl, aryloxy, halogen, hydroxy, sulfonamide, carboxy or phosphonate.

One such compound, a condensation polymer of formaldehyde and naphthalenesulfonic acid (PIC 024.4), can alternatively be isolated from dye compositions such as Direct Yellow 29, a commercial dye comprising a mixture of several compounds wherein the compound of interest was added as a dispersant. Prior to formulation in a suitable physiologically acceptable vehicle, the preparation can be purified using known purification techniques, such as precipitation, crystallization, extraction and/or chromatography to isolate PIC 024.4. An example of the latter of these is described in detail in the exemplification.

The condensation polymers employed herein can, preferably, be fractionated to obtain novel narrow or mono-dispersed molecular weight condensation polymers, possessing superior properties over the polydispersed polymers of U.S. Pat. No. : 4,604,404.

In general, as the molecular weight of the polymer increases, the therapeutic activity of the polymer or number of sulfonic acid groups increases. However, the anticoagulation activity of the polymer also increases. Accordingly, the molecular weight and sulfonic acid concentration are advantageously chosen to achieve optimal antiviral activity while minimizing the anticoagulation effect.

Employing these principles, the polymer can be selected which achieves a preferred therapeutic ratio. "Therapeutic ratio" is defined herein as the dosage (μg/ml) required to achieve an average anticoagulation doubling time of the upper normal partial thromboplastin time, employing the anticoagulation assay set forth below, divided by the dosage (μg/ml) required to achieve fifty percent inhibition of CD4-gp120 binding in the cellular assay, set forth below. The preferred therapeutic ratio is at least about 7, most preferably at least about 20.

It is preferred that the peak molecular weight ($M_p$) be less than about 50 kDa and/or greater than about 0.7 kDa. More preferred are polymers with a peak molecular weight between from about 1.3 to about 30 kDa, most preferred between from about 4 to about 12 kDa. A particularly advantageous polymer is a 5±1 kDa condensate of 2-naphthalene sulfonic acid and formaldehyde, termed PRO-2000 or PRO 2000/5 herein.

Preferably, the average number of sulfonic acids per aromatic group is between about 0.5 to about 2.0, most preferably about 1.0.

The narrow or mono-dispersed molecular weight polymers can be prepared by fractionation methods generally known in the art (see, e.g., *Polymer Fractionation*, Editors, Cantow and Manfred, Jr., (Acad. Press) 1967), such as solvent precipitation, gel permeation chromatography, salt precipitation and diafiltration. Alternatively, the polymers can be manufactured by the stepwise or controlled condensation of naphthalenesulfonic acid and formaldehyde. A "narrow-dispersed polymer" is defined as a polymeric composition wherein the species thereof possess substantially the same molecular weight. For example, a narrow-dispersed polymer includes polymeric compositions wherein substantially all species thereof have a molecular weight within about ±3 kDa, preferably about ±2 kDa and more preferably about ±1 kDa of the mean molecular weight of the composition. A "mono-dispersed polymer" is defined as a polymeric composition wherein substantially all of the species thereof possess a single molecular weight, such as a tetramer, pentamer, hexamer, heptamer, octamer, nonamer, etc.

The disclosed polymers abrogated CD4/gp120 binding in a primary binding assay. The polymers showed antiviral activity against HIV strains HTLV-IIIB, JR-CSF, ADA and others, in in vitro assays. Furthermore, the polymers were found to be specific and with little to no cytotoxicity, failing to show significant activity against CD2/LFA-3 interaction and T-cell proliferation or toxicity against a variety of cell lines tested. From this data, more specifically set forth below, it is concluded that condensation polymers of the type herein described are active as antiviral agents against the virus, HIV.

Based upon the results discussed herein, a preparation containing condensation polymers of formaldehyde and aromatic sulfonic acids, such as PRO 2000/5, PRO 1041 and PRO 1135, can block CD4 mediated steps of HIV infection. As such, they can be used to treat individuals infected with many, if not all, strains of HIV, in vivo (e.g., by administration to infected or exposed individuals and individuals who test positive for HIV antibodies but remain asymptomatic). The compounds are active against CD4-mediated infection by non-syncytia inducing (NSI) and syncytia inducing (SI) phenotypes of the HIV virus. It can also be used prophylactically for uninfected or potentially exposed individuals (such as, following needle stick accidents and newborns of infected mothers. The preparation can be used to inhibit binding of HIV to CD4 lymphocytes and to inhibit transmission of virus from an infected cell to uninfected cells including HIV infection mediated by syncytia formation. As the compound inhibits the binding of HIV to CD4, and is an immune system specific intervention, it is not expected to lead to viral resistance.

As described above, the condensation polymer can, optionally, be administered as a pharmaceutically acceptable salt. Examples of suitable salts include the alkaline, alkali metal and ammonium salts, such as calcium, sodium and ammonium salts.

Additionally or alternatively, the polymer can be administered as a prodrug, thereby improving the bioavailability of the polymer. Prodrugs of the polymer include polymers wherein one or more sulfonic acid groups are derivatized or blocked such that, upon administration the blocking group is removed in vivo, yielding the active sulfonic acid group. For example, the sulfonic acid group can be esterified by reacting the acid with the corresponding alcohol. Suitable alcohols include linear or branched alkanols (such as ethanol, t-butanol and neopentanol). The prodrug is preferably cleaved in vivo by, for example, enzymatic hydrolysis. Furthermore, the blocking group is preferably selected to minimize any toxicity yielded by its in vivo removal.

The preparation or polymer of this invention can be administered intravaginally or rectally (e.g., contraceptive formulation, suppository or lubricant), orally (e.g., capsule, tablet or liquid formulation), parenterally (e.g., intramuscularly, intravenously, subcutaneously), topically, nasally or via slow releasing microcarriers in dosage formulations containing a physiologically acceptable vehicle and optional adjuvants and preservatives. Suitable physiologically acceptable vehicles include saline sterile water, Ringer's solutions, and isotonic sodium chloride solutions. Specifically, Sodium Chloride Injection USP (0.9%), Ringer's Injection USP, Lactated Ringer's Injection USP, Sodium Lactate Injection USP, Dextrose Injection USP (5% or 10%), Bacteriostatic Water for Injection USP and Sterile Water for Injection USP can be used, for example. Advantageously, the compounds can be administered in a contraceptive formulation, such as a contraceptive gel, cream or foam. The specific dosage level of active ingredient will depend upon a number of factors, including biological activity of the particular preparation, age, body weight, sex, general health and the clinical stage of AIDS in the patient or individual.

Other antiviral agents which interfere with HIV viral replication can be administered in conjunction with this preparation, according to the methods of this invention with synergistic results in some instances. Co-administration of antiviral agents can effectively inhibit various stages of the virus life cycle, thus optimizing the therapeutic benefit of the preparation of this invention, for reducing or eliminating viral infectivity and the symptoms associated therewith. For example, HIV reverse transcriptase inhibitory agents (such as, azidothymidine (AZT) or dideoxyinosine (ddI)), uncoating inhibitors (bicyclam), integration, transcription, or translation inhibitors (antisense oligonucleotides), other fusion/binding inhibitors, assembly/release inhibitors (e.g., IFN), HIV protease inhibitors, or non-nucleoside reverse transcriptase inhibitors (such as, nevirapin) can be co-administered with the condensation polymer separately or as a single dosage formulation containing the condensation polymer and other anti-viral agent(s).

The polymer can also be administered in conjunction with or chemically linked to a suitable targeting agent for $CD4^+$ cells, such as a T-cell antibody.

Additionally, the compound can be added to a blood preparation in vitro. In this embodiment the compound effectively blocks viral binding and entry into $CD4^+$ cells, preventing infection of T-cells. The compound can be added to the blood preparation alone or in combination with a suitable vehicle, such as sterile saline water, Ringer's solution or isotonic sodium chloride solutions, for example. The effective amount required will depend upon a number of factors, including the particular blood preparation, and the vehicle chosen.

The invention will be further illustrated by the following non-limiting exemplification:

1. SYNTHESIS AND ISOLATION OF CONDENSATION POLYMERS 1.1 Isolation and Characterization of PIC 024.4

A solution of Direct Yellow 29 (Aldrich Chemical Company, lot #0033187; Sigma Chemical Company, lot # 17F3484), was prepared by dissolving 10.0 g in 200 ml of water, the solution was acidified with trifluoroacetic acid (0.1% trifluoroacetic acid final concentration) and stirred for one hour at 4° C. The precipitate was removed by filtration and the filtrate was subjected to preparative high pressure liquid chromatography (HPLC) using a Waters 600E system equipped with PrePak® RCM cartridge column assembly (Waters Chromatography, Division of Millipore, Milford, Mass.). The mobile phase consisted of 0.1% trifluoroacetic acid in water (solvent A) and 0.1% trifluoroacetic acid in acetonitrile/water (60:40) (solvent B). With an initial solvent mixture of 70% solvent A; 30% solvent B and a flow rate of 25 ml/min, the stock solution (5 ml) was loaded onto a 40×300 mm DeltaPak™ $C_{18}$ column (particle size=15 μm, mean pore diameter=300 Å). The concentration of solvent B was increased to 70% at a rate of 1.2%/min and then to 100% at a rate of 15%/min. Monitoring at 280 nm, the material eluting between 10.0 and 21.8 minutes was collected and concentrated to afford PIC 024.4.

PIC 024.4 was characterized by a variety of techniques such as HPLC, NMR, IR, UV and fluorescence determinations.

$^1$H NMR spectrum (250 MHz Bruker, DMSO-$d_6$) of PIC 024.4 was comprised of the following peaks: δ 6.5–8.6 (br m), 4.8–5.0 (br s), 4.2–5.0 ppm (br s).

In the IR of PIC 024.4 (FT, Perkin Elmer, KBr), 3448, 1630, 1400, 1186, 1122, 1030 and 680 $cm^{-1}$ were the main peaks.

1.2 Synthesis of Condensates: Polymerization

A mixture of 2-naphthalenesulfonic acid sodium salt (1.15 g, 5 mmol), 37% aqueous formaldehyde (0.65 ml, ~6 mmol), and sulfuric acid (0.7 g concentrated sulfuric acid in 0.5 ml of water) was heated at 980 to 100° C. for 43 hours. The reaction mixture was then diluted with water (30 ml), neutralized with calcium carbonate to pH 7 and filtered, the filtrate was evaporated to dryness to yield 1.22 g of the condensate PRO 1041.

$^1$H NMR and IR of this product was found to be similar to PIC 024.4 reported above.

The above experiment was repeated modifying the reaction parameters as exemplified in Table 1.

TABLE 1

| Reaction | HCHO (eqv) | Water (ml) | Temp (° C.) | Time (h) | Product size (kDa) | | |
|---|---|---|---|---|---|---|---|
| | | | | | Mp | MWd | MW |
| PRO 1041* | 1 | 0.5 + 1 | 96–104 | 45 | 6.0 | 0.7–150 | 16 |
| PRO 1077* | 1 | 1.5 + 0.5 | 103–107 | 52 | 25 | 0.2–100 | 13 |
| PRO 1078* | 1 | 2 + 0.5 | 100–103 | 54 | 2.0 | 2–200 | 12 |
| PRO 1079* | 1 | 2 + 1 | 100–105 | 44 | 0.4 | 0.3–175 | 9 |
| PRO 1080 | 1 | 1.5 | 95–100 | 44 | 2.0 | 0.4–90 | 9 |
| PRO 1081 | 1 | 1.5 | 100–105 | 53 | 4.0 | 0.4–100 | 14 |

TABLE 1-continued

| | HCHO | Water | Temp | Time | Product size (kDa) | | |
|---|---|---|---|---|---|---|---|
| Reaction | (eqv) | (ml) | (° C.) | (h) | Mp | MWd | MW |
| PRO 1082 | 1 | 2 | 105–110 | 92 | 8.0 | 3–100 | 14 |
| PRO 1083 | 1 | 0.5 | 96–105 | 72 | 21 | 0.1–980 | 56 |
| PRO 1121 | 1 | 1.5 | 120–125 | 6 | 0.2 | 0.2–10 | 2 |
| PRO 1122 | 1 | 1.5 | 120–125 | 8 | 0.2 | 0.3–15 | 2 |
| PRO 1133 | 1 | 1.5 | 120–125 | 15 | 3.0 | 0.3–100 | 4 |
| PRO 1135 | 1 | 1.0 | 120–125 | 8 | 3.0 | 0.4–80 | 14 |
| PRO 1075 | 0.5 | 1.5 | 98–100 | 48 | 3.0 | 0.4–100 | 11 |
| PRO 1076 | 0.75 | 1.5 | 98–100 | 24 | 4.0 | 1–120 | 18 |

*Open vessel reactions;
Mp = peak molecular weight;
MWd = molecular weight distribution;
MW = molecular average weight

1.2.1 Synthesis of PRO 2000

A mixture of 5.7 g of 2-naphthalenesulfonic acid, sodium salt (23 mmol) was combined with ~3 ml of 37% formaldehyde (~43 mmol), 1.9 ml of concentrated sulfuric acid, and 5 ml of water was combined and heated in a sealed tube for ~24 hours at 120–130° C. The reaction mixture is diluted with water (~20 ml) and neutralized to pH=7 with NaOH. The neutralized reaction can be concentrated to dryness to obtain ~11 g, which consists of the condensate and salts.

1.3 Characterization of PIC 024.4 and PRO 1041

1.3.1 Reverse Phase High Pressure Liquid Chromatograph (RP-HPLC):

PRO 1041 were subjected to analytical HPLC using a Waters 625 pump/490 detector/Satellite WISP system equipped with a Zorbax RX-C18 column (4.6×150 mm, 5 $\mu$M particle size, 90A pore size) (MAC-MOD Analytical, Chadds Ford, Pa.). The mobile phase consisted of 0.1% trifluoroacetic acid in water as solvent A and 0.1% trifluoroacetic acid in acetonitrile/water (60:40) as solvent B. The samples were injected at an initial solvent mixture of 90% solvent A: 10% solvent B and a flow rate of 1 ml/min. The concentration of solvent B was increased to 100% at a rate of 2.5%/min. and elution monitored at 233 nm. PIC 024.4 and PRO 1041 exhibited similar chromatographic profiles.

1.3.2 UV Absorption Spectra

UW spectra were recorded at 20° C. over the wavelength range 200 to 350 nm, with a spectral resolution of 1 nm, for both samples of PRO 1041 and PIC 024.4 at concentrations of approximately 2 $\mu$g/ml, in phosphate buffered saline (PBS), pH 7.4. The spectrophotometer was a Perkin Elmer Lambda 6 and a 1 cm pathlength cuvette was used.

The spectra for both PRO 1041 and PIC 024.4 had a maximum at 228 nm. Smaller bands at 296 nm with shoulders at 330 nm where also present in the spectra of both compounds.

1.3.3 Fluorescence Spectroscopy

Fluorescence emission spectra were recorded at 20° C. over the wavelength range 320 nm to 500 nm with a spectral resolution of 2 nm for PRO 1041 in PBS at a concentration of approximately 2 $\mu$g/ml. The spectrofluorimeter was a SLM-Aminco SPF500C and the excitation wavelength was 300 nm having a bandpass of 4 nm. A 0.5 cm pathlength cuvette was used and the volume was 500 $\mu$l.

PRO 1041 and PIC 024.4 had closely similar emission spectra having a maximum intensity at ~355 nm.

Based on the studies described in this exemplification PIC 024.4 was identified as a naphthalenesulfonic acid formaldehyde condensate, a polymeric dispersant additive to the dye, possessing the identifying characteristics of PRO 1041.

1.4 Synthesis of Condensates: Stepwise

1.4.1 5-Bromo-2-naphthalenesulfonic acid

5-Amino-2-naphthalenesulfonic acid (11.15 g, 50 mmol) was dissolved in 100 ml of 0.5 N NaOH solution with stirring. The dark-red solution was cooled down to 0° C. by addition of ice (~100 g). Before the ice completely dissolved, 20 ml of 40% HBr aqueous solution was added dropwise and the resulting suspension was maintained at ~5° to 0° C., then 10 ml of $NaNO_2$ (3.65 g) aqueous solution was added in 30 minutes. The mixture was stirred continuously for 30 minutes at −5°~0° C. The unreacted $NaNO_2$ was decomposed by addition of 350 mg of urea at the end of reaction. The resulting dark diazonium suspension was kept below 0° C., and added dropwise over one hour period to CuBr (7.15 g) solution in 40 ml of 40% HBr at 70° C. with vigorous stirring (the CuBr solution was in a 1000 ml flask). The dark mixture was stirred at 80° C. for 40 minutes, then cooled down to room temperature and added with 200 ml of water. The precipitate was collected in Buchner funnel and washed with about 50 ml of water. 13.9 g of crude product was obtained after drying under vacuum. The crude compound was refluxed in 500 ml of water for 2 hours, cooled to room temperature and filtered. The filtrate was evaporated to dryness and solid dried in vacuo to yield 8.23 g (57% yield) of pure product.

The purity of product was checked with reverse phase HPLC and $^1$H-NMR (250 MHz).

1.4.2 8,8'-Methylen-bis-5-bromo-2-naphthalenesulfonic acid (sodium salt)

A mixture of 5-bromo-2-naphthalenesulfonic acid (17.22 g), TFA (200 ml), Amberlyst-15 resin (17 g, Aldrich), paraformaldehyde (4.5 g) and $H_2O$ (50 ml) was heated at 130° C. for 14 hours in a closed thick-wall tube. After cooling to room temperature, the mixture was filtered in a Buchner funnel and, the collected solid was washed with about 10 ml of TFA, dissolved in 250 ml of methanol/water (4/1) and filtered. The filtrate was evaporated to dryness and the solid was suspended in 80 ml of water, neutralized to pH ~8 with 10 M NaOH. The solid was filtered, washed with 60 ml of acetone and dried in vacuo overnight. 15.03 g (80% yield) of pure product was obtained.

1.4.3 8,8'-Methylen-bis-2-naphthalenesulfonic acid

A suspension of 8,8'-methylen-bis-5-bromo-2-naphthalenesulfonic acid (sodium salt, 6.30 g), NaOH (0.32 g) in 300 ml of MeOH, was slowly added with Pd—C (10%, 5.0 g) under argon atmosphere. The suspension was shaken at 50 psi of $H_2$ for 18 hours. Then the mixture was filtered and the filtrate was passed through a column packed with ~20 g of IR-120 resin. The solvent was removed on rotavap, and the residue was dissolved in 200 ml of water then filtered again. The filtrate was neutralized with 5 M NaOH to pH ~7 and concentrated to ~50 ml volume, then 300 ml of acetone was added slowly with shaking. The resulting white precipitate was collected in Buchner funnel, washed with 20 ml of acetone and dried in vacuo to result 3.51 g of dry product (sodium salt).

1.4.4 Oligomerization for Tetramer and Hexamer 5.11 g of sodium salt of dimer was converted into free acid by passing through IR-120 resin column in water. Water was removed on rotavap and the residue was again dissolved in 10 ml of water and transferred into 50 ml of TFA in a thick-wall flash, then paraformaldehyde (0.195 g) was added and the flask was sealed. The solution was stirred at 60° C.–65° C. for 15 hours. The solvent was removed and the residue was dissolved in methanol, coated on silicon gel and subjected to flash silicon-gel column (EM Science, silica gel 60 F-254, 230–400 mesh for column), where the elution was started with 16:1:1 of THF:MeOH:$H_2O$ to 5:1:1 final ratio.

The solid from tetramer fraction (PRO 1072) was neutralized to pH ~7 with 5 M NaOH in 5 ml of water, added with 5 ml of MeOH and 125 ml of acetone to afford 0.94 g of precipitate. The salt was converted into free acid by passing through IR-120 resin and 0.73 g of dry tetramer was obtained.

From the hexamer fraction, 0.21 g of hexamer (PRO 1073) was obtained by the same method as that described for tetramer.

3.5 g of starting material (dimer) was recovered from the first fraction.

1.4.5 Octamer: PRO 1191

A mixture of tetramer (130 mg), Amberlyst-15 resin (150 mg), water (0.4 ml), and 2 ml of TFA solution of paraformaldehyde (1 mg/ml) was stirred at 85° C. for 15 hours in a sample vial closed with a teflon cap. The reaction mixture was cooled to room temperature, diluted with 5 ml of water and filtered. The filtrate was evaporated to dryness, dissolved in methanol, and coated on silica gel, then passed through a flash column where tetramer was eluted with 6:1:1 of THF:isopropanol:$H_2O$, and octamer was eluted with MeOH:$H_2O$ (85/15). From later fraction 50 mg of crude octamer was obtained.

The crude octamer was passed through IR-120 resin, purified by reverse phase prep HPLC and 15 mg of octamer (96.6% pure by analytical HPLC) was obtained.

1.5 Size Exclusion Chromatography

Aliquots of synthetic polymer solutions were fractionated by size using a Waters M625 pump, M996 diode array detector, Millenium software system and either two 6 $\mu$m 250 angstrom Waters Ultrahydrogel columns (7.8×300 mm; mobile phase flow 1 ml/min) or a 17 $\mu$m TosoHaas G3000PW column (21.5×600 mm) coupled with a TSK-Gel Guard PWH column (21.5×75 mm; flow rate 3 ml/min). The mobile phase consisted of 0.2 M ammonium acetate (pH 6.2) made from glacial acetic acid (Baker Analyzed HPLC Reagent) and ammonium hydroxide (25%, Mallinckrodt)- and 35% acetonitrile (B&J Brand). Prior to use, the mobile phase was filtered through a 0.45 $\mu$m nylon membrane and sparged under Grade 5 helium. A solution of the synthetic samples at 2.2–10 mg in up to 200 $\mu$l MilliQ water was injected onto the Ultrahydrogels or 40–300 mg in up to 2 ml MilliQ watermobile phase (50:50, v/v) was injected onto the TosoHaas columns following ultrasonicating (Branson 2200), vortexing and filtering (0.45 $\mu$m Acrodisc, Gelman Sciences). Collected fractions were pooled according to elution time. Superimposable chromatographic profiles by absorbance measurements were demonstrated with replicates- and the solvent was removed using Savant speed-vacs at high temperature (either SC200 and Vapornet VN100 or Plus SC210A). The residue was redissolved in water and redried for removing trapped solvent. The material was weighed, dissolved in water and normalized to stock concentrations using absorbance measurements at 290 nm versus standards.

PRO 1135 was fractionated in this manner to obtain polymer fractions possessing a peak molecular weight (Mp) of 31 kDa (average molecular weight (MW) of 38 kDa); an Mp of 16 kDa (MW of 22 kDa); an Mp of 10 kDa (MW of 15 kDa); and an Mp of 5.6 kDa (MW of 10 kDa).

1.5.1 Light Scattering Methodology

The samples were subjected to analytical HPLC using a Waters 625 pump/modified 410 RI detector that contained inside a PD2000 laser light scattering intensity detector (Precision Detectors, Inc., Amherst, Mass.). This system was equipped with a Waters Ultrahydrogel 250 aqueous GPC column (7.8 mm I.D.×300 mm, 250 Å pore size, 8×$10^4$ exclusion limit, PEO). The mobile phase consisted of 65% 0.2M ammonium acetate pH=6.5/35% acetonitrile in an isocratic mode with a flow rate of 1 ml/min. Elution was monitored by RI, low (15°) and high (90°) angle light scattering and absolute molecular weight ranges were obtained from this information.

1.6 PRO 2000 Fractionation

The salts from the neutralization process were removed through a fractionation process by addition of a polar organic solvent (acetone, ethanol, or methanol). An aqueous solution of the final reaction mixture (~10 g/20 ml) was treated with incremental amounts of organic solvents. Initial organic solvent caused the dissolved salts to form a lower layer.

Once the majority of the salt was removed, fractionation of the material into more homogeneous molecular weight ranges occurs. Additional solvent was added to form a lower, darker layer. The volume of organic solvent added was determined by monitoring the two phases by GPC/LS. In general, the higher molecular weight material was moved into the lower layer and the lower molecular weight material remained in the upper layer.

When the desired molecular weight range was identified, it was isolated in one of several ways. The first method was to simply remove all volatile solvent from the material (by a combination of rotary evaporation under reduced pressure and vacuum oven). The second method was to disperse the solution of the product into a large excess of a polar organic solvent (acetone, ethanol, or methanol) and collect the resulting solid by filtration.

Material prepared according to the above reaction description and fractionation process yielded several narrow range molecular weights (~3K, ~5K, ~10K, ~25K, PRO 2000/3, 2000/5, 2000/10 and 2000/25, respectively).

2. MICROBIOLOGICAL ACTIVITY 2.1 Molecular Binding Interactions 2.1.1 Demonstration of Binding to CD4

Fluorescence emission spectra of PIC 024.4, PRO 1041 and PRO 1135 and PRO 2000 fractionation products were recorded using an excitation wavelength of 315 nm as described above. Wild type 2 domain recombinant CD4 (20 $\mu$l of a 130 $\mu$M stock solution in PBS) was then added to a final concentration of 5 $\mu$M and the measurements were repeated. An excitation wavelength of 315 nm ensured that no inner filter effect, nor fluorescence signal, was contributed by the added protein. Furthermore, the low concentrations of the reagents employed excluded significant collisional fluorescence quenching. Therefore, the observation of 60–70% quenching of the fluorescence signals for PRO 1041 in the presence of CD4 protein, provided evidence for binding to the receptor.

The fluorescence quenching experiment provided direct evidence that PIC 024.4 bind tightly to CD4. The fluorescence emission spectrum of the polymer at 0.6 µg/ml was determined in the absence and presence of 5 µM recombinant CD4. Addition of CD4 quenched the intrinsic fluorescence of PIC 024.4 in a saturable manner, indicating direct binding to the protein. An excitation wavelength of 315 nm ensured that no inner filter effect, nor fluorescence signal, was contributed by the added protein. Furthermore, the low concentrations of both reagents excluded significant collisional fluorescence quenching.

2.1.2 Direct binding of PRO 2000 fractions to CD4

The binding of CD4 to each of the PRO 2000 fractions was also studied. Solutions of each fraction (~200 nM based on the average molecular weight) were titrated with soluble CD4, and the fluorescence measured at 355 nm (following excitation at 315 nm). The fraction of polymer bound was calculated from these data and plotted as a function of CD4 concentration. For each fraction, a nonlinear curve fit was used to obtain a dissociation constant ($K_d$) and a binding stoichiometry (n). The results are shown in Table 2 and, FIGS. 14A and 14B. All of the fractions bound to CD4 with high affinity, and with a stoichiometry of about one polymer per CD4 molecule. The differences in the measured $K_d$ values are probably not significant. Similar $K_d$ values were measured in preliminary SPR biosensor experiments, in which the PRO 2000 fractions were allowed to bind to CD4 immobilized to the sensor surface.

TABLE 2

Direct binding of PRO 2000 fractions to CD4.

| Fraction | $K_d$ (nM) | n |
|---|---|---|
| PRO 2000/3 | 25 | 1.2 |
| PRO 2000/5 | 16 | 1.0 |
| PRO 2000/10 | 46 | 0.7 |
| PRO 2000/25 | 59 | 0.5 |

2.1.3 CD4/gp120 Binding Assay: Cellular

CEM cells (a human T-cell leukemia line available from the American Type Culture Collection, Rockville, Md.; $3 \times 10^6$ cells per ml) were suspended in RPMI 1640 (Whittaker-Bioproducts, Walkersville, Md.) with 10% fetal bovine serum (FBS) (JRH Biosciences, Lenexa, Kans.) plus 0.1% sodium azide. 100 µl of the suspension were added to each tube. Generally, the test compounds were dissolved in water to a final concentration of 4 mg/ml. Various dilutions (1:40, 1:100, 1:200) of PIC 024.4, PRO 1041, fractionated PRO 1135 or PRO 2000 were added to the tubes and incubated for 2 hours at 25° C. Next, gp120 (American Bio-Technologies, Inc., Cambridge, Mass., diluted in RPMI 1640 buffer, was added to a final concentration of 10 nM. The solution was then incubated overnight (~16 hours) at 37° C.

Cells were washed thoroughly with phosphate-buffered saline (PBS) containing 10% FBS and 0.1% sodium azide. To reveal bound gp120, monoclonal antibody specific for gp120 (NEN-Dupont, NEA-9284) was then incubated with the cells at a concentration of 1 µg/ml (100 µl per tube) for 30 minutes on ice. The cells were washed thoroughly as before and stained with goat anti-mouse immunoglobulin (Boehringer Mannhein Biochemicals, Indianapolis, Ind.) which was labeled with fluorescein (50 µl per tube) for 30 minutes on ice. The washed cells were analyzed for fluorescence on a FACScan™ (Becton Dickinson).

2.1.4 Inhibition of gp120 binding to CD4-expressing CEM cells

This assay was used to measure the ability of test compounds to inhibit the binding of recombinant gp120 to the CD4 receptor expressed on the surface of lymphocytic cells. Cells of the CEM line (a CD4+ human T cell leukemia line) were suspended at $3 \times 10^6$ cells/ml in RPMI 1640 medium supplemented with 10% fetal bovine serum (FBS) containing 0.002% sodium azide, and 100 µl was aliquoted to individual assay tubes. Serial dilutions of test compound in water were added (10 µl/tube) and the tubes incubated for 2 hours at 25° C. Next, recombinant gp120 (IIIB isolate) diluted in RPMI 1640 buffer was added to a final concentration of 10 nM (1.2 µg/ml) and the tubes incubated overnight at 37° C. Cells were then washed thoroughly with PBS containing 10% FBS and 0.01% sodium azide. V3-specific monoclonal antibody NEA9284 was added to a concentration of 1 µg/ml and incubated for 30 minutes on ice. The cells were washed thoroughly as before and stained with fluorescein-labeled goat anti-mouse immunoglobulin for 30 minutes on ice. The washed cells were analyzed for mean fluorescence on a FACScan™ flow cytometer (Becton Dickinson). Percent inhibition of fluorescence was determined relative to cells that were not treated with drug.

The $IC_{50}$ for PIC 024.4 in this experiment was 3.5 µg/ml (FIG. 12). In a parallel experiment, dextran sulfate (8 kD) showed an $IC_{50}$ of 23 µg/ml. In this case, inhibition may have resulted from interference with binding of the probe antibody—dextran sulfate has been shown to block the binding of antibody NEA 9284 to gp120, Lederman et al., *AIDS Res. Hum. Retroviruses* 8:1590–1610 (1992).

All four PRO 2000 fractions inhibited the binding of recombinant gp120 to CEM cells (FIG. 13). $IC_{50}$ values ranged from ≦1.4 to 4.9 µg/ml. The potencies of the 5-, 10- and 25-kD fractions were similar, though the 3-kD fraction inhibited somewhat more weakly. As with PIC 024.4, the $IC_{50}$'s were higher than those measured in the ELISA. This difference does not appear to be due to the fact that different probe antibodies were used—$IC_{50}$'s in the CEM assay were identical when the ELISA probe (NEA 9205) was used.

The octamer (PRO 1191), hexamer (PRO 1073), tetramer (PRO 1072) and dimer (PRO 1055) were also tested in this assay. Average $IC_{50}$'s from several experiments were 8, 24, 33, and 660 µg/ml, respectively. Data from a representative experiment are shown in FIG. 13B.

2.1.5 CD4gp120 Binding Assay: ELISA

The ELISA (Dupont NEN, Boston, Mass.) utilized a 4-domain soluble CD4 (sCD4) purified from Chinese hamster ovary cells which was immobilized to a 96-well microtiter plate. Fifty µl of gp120 (1 ng at 20 ng/ml) and 50 µl of active compound at appropriate concentrations were added to the microtiter plate in duplicate and incubated overnight at 4° C. The plate was washed 6 times with Wash buffer (2 mg/ml BSA/PBS) and 100 µl anti-gp120 monoclonal antibody-horseradish peroxidase (HRP) conjugate was added. The plate was incubated 2 hours at 4° C., washed 6 times with Wash buffer and developed with 100 µl ortho phenylenediamine (OPD) substrate solution for 30 minutes at 25° C. A dose-response curve with increasing concentrations of soluble, baculovirus-derived gp120 (HIV-1 IIIB strain) was prepared which illustrated that half-maximal binding occurred at a concentration of 20 ng/ml as detected by HRP-conjugated anti-gp120 monoclonal antibody specific for residues 308–322 on gp120. Therefore, varying concentrations of polymer were incubated in the presence of a constant amount of gp120 (1 ng at 20 ng/ml) to assess inhibition of CD4/gp120 interactions.

The $IC_{50}$'s for polymers tested in the ELISA are summarized in Table 3. The activity for PIC 024.4 in both the ELISA and cellular assays are summarized in Table 4, FIGS. 1 and 12.

TABLE 3

| Polymer | Product size (kDa) | | | IC$_{50}$ |
|---|---|---|---|---|
| | Mp | MWd | MW | (ug/ml) |
| PRO 1041 | 6.0 | 0.7–150 | 16 | 0.05 |
| PRO 1077 | 25 | 0.2–100 | 13 | 0.10 |
| PRO 1078 | 2.0 | 2–200 | 12 | 1.0 |
| PRO 1079 | 0.4 | 0.3–175 | 9 | 1.5 |
| PRO 1080 | 2.0 | 0.4–90 | 9 | 0.9 |
| PRO 1081 | 4.0 | 0.4–100 | 14 | 0.25 |
| PRO 1082 | 8.0 | 3–100 | 14 | 0.10 |
| PRO 1083 | 21 | 0.1–980 | 56 | 0.07 |
| PRO 1121 | 0.2 | 0.2–10 | 2 | 70 |
| PRO 1122 | 0.2 | 0.3–15 | 2 | 20 |
| PRO 1133 | 3.0 | 0.3–100 | 4 | 20 |
| PRO 1135 | 3.0 | 0.3–80 | 14 | 0.55 |
| PRO 1075 | 3.0 | 0.3–100 | 11 | 0.70 |
| PRO 1076 | 4.0 | 1–120 | 18 | 0.18 |

TABLE 4

| PIC 024.4 Concentration* | % Inhibition CD$_4$/gp120 | |
|---|---|---|
| (µg/ml) | ELISA | Cellular |
| 100 | | 99 |
| 40 | | 97 |
| 20 | | 89 |
| 10 | 90 | 51 |
| 5.0 | — | 27 |
| 2.5 | — | 12 |
| 1.0 | 77 | — |
| 0.1 | 43 | — |
| 0.01 | 2 | — |

*30% naphthalene sulfonic acid condensate by weight 2.1.6 CD4/gp120 Binding Assay ELISA This ELISA system, similar to that described above (2.1.5), was used to assess the effect of test compounds on the binding of recombinant gp120 to recombinant CD4 absorbed to polystyrene. Polystyrene 96-well microtiter plates were treated with a 1 µg/ml solution of recombinant, soluble four-domain CD4 (sCD4) expressed in insect cells (100 µl/well) and allowed to incubate for two hours at room temperature. Plates were blocked for two hours at 4° C. with phosphate-buffered saline (PBS) containing 0.05% Tween-20 and 10 mg/ml bovine serum albumin (PBSTB, 200 µl/well), and then washed five times with PBS containing 0.05% Tween-20. Fifty microliters of 60 ng/ml recombinant gp120 (IIIB isolate) and 50 µl of each drug dilution in PBSTB were added to duplicate wells, and the plate was incubated overnight at 4° C. The plate was then washed five times with PBST and treated with a 210 µg/ml solution of monoclonal antibody NEA 9205 (100 gp120-III/well). This antibody recognizes the V3 loop region of gp120-IIIB. After incubation for 2 hours at 4° C., the plate was washed five times with PBST and treated with an anti-mouse IgGl antibody conjugated to alkaline phosphatase. After an additional incubation for 1 hour at 4° C., the plate was washed five times with PBST, treated with a p-nitrophenyl phosphate substrate solution, incubated for about 30 minutes at room temperature, and monitored for color development at 405 nm. Percent inhibition of color development relative to untreated control wells was calculated for each dilution of drug, and a plot of percent inhibition versus log concentration was used to determine at 50% inhibitory concentration (IC$_{50}$). Aurintricarboxylic acid was used as a positive control. IC$_{50}$ values for six replicates of a PRO 2000/5 solution showed a standard deviation of 25%. IC$_{50}$ values reported here were similar to those reported above.

Figure 9:
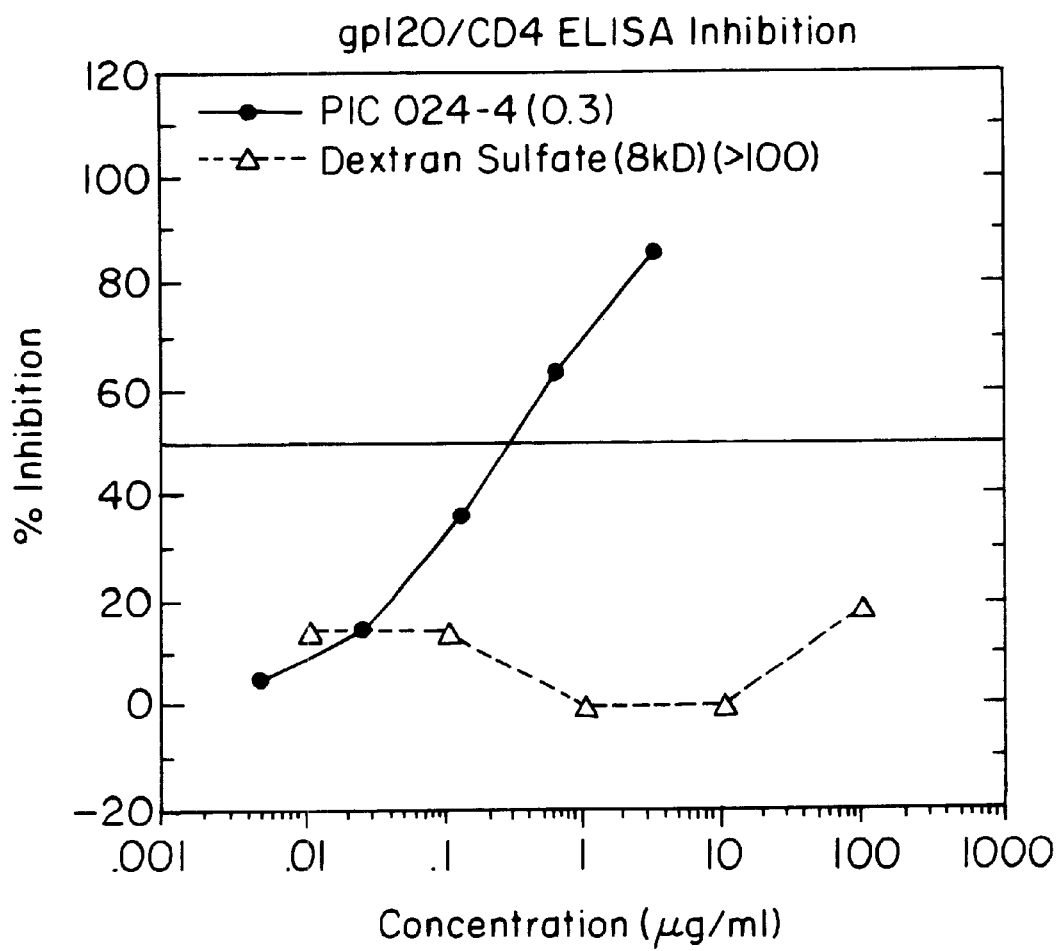
FIG. 9 is a graphic illustration of the inhibition of gp120 binding to recombinant CD4 in an ELISA format for PIC 024.4 (closed circles), dextran sulfate, 8 kD (open triangles). $IC_{50}$'s (in μg/ml) are parenthesized.

PIC 024.4 was shown to inhibit the binding of recombinant gp120 to recombinant CD4 in this ELISA format. The IC$_{50}$ measured using this system was 0.3 µg/ml (FIG. 9). Aurintricarboxylic acid, which has been reported to inhibit the binding of gp120 to CD4 (Chou et al., *AIDS Res. Hum Retroviruses* 9:541–546 (1993)), gave an IC$_{50}$ of ~1 µg/ml. By contrast, an 8-kD preparation of dextran sulfate, which has been evaluated as an antiviral agent in humans (Flexner et al., *Antimicrob. Agents Chemother.* 35:2544–2550 (1991)), was inactive in the ELISA (FIG. 9).

All four PRO 2000 fractions inhibited recombinant gp120 binding to recombinant CD4 by ELISA (FIG. 10). IC$_{50}$ values ranged from 0.12 to 1.1 µg/ml, with potency increasing with average molecular weight in the order 25 kD≈10 kD>5 kD>3 kD. Inhibition curves for repeat assays on the same fractions suggest that these differences are significant.

The octamer (PRO 1191), hexamer (PRO 1073), tetramer (PRO 1072) and dimer (PRO 1055) were also tested in this assay. In several experiments, the average IC$_{50}$'s were 5, 250, >210, and 410 µg/ml, respectively. Data from a representative experiment are shown in FIG. 10B. Note that the octamer is significantly more potent than the other fractions in this assay.

2.1.7 Inhibition of CD2 binding to CD58 by ELISA (specificity control)

This assay was used to assess the effect of test compounds on the binding of CD2 to its ligand, CD58 (LFA-3). Like CD4, CD2 is a T lymphocyte receptor protein and a member of the immunoglobulin superfamily. The ELISA utilizes a recombinant, soluble CD58 and a recombinant CD2-IgM chimera (Arulanandam et al., *J. Exp. Med.* 177:1439–1450 (1993)), both expressed in CHO cells. Polystyrene 96-well microtiter plates were treated with CD58 and then blocked with PBS containing 2% BSA (PBSB). Plates were then washed thoroughly, treated with serial dilutions of PRO 2000 (50 µl/well) and a 0.1 µg/ml solution of CD2-IgM in PBSB (50 µl/well), and incubated overnight at 4° C. The plate was then washed three times with PBSB, treated with mouse anti-human IgM-alkaline phosphatase conjugate (100 µl/well), and incubated one hour at 25° C. The plate was washed again three times and treated with p-nitrophenyl phosphate substrate (100 µl/well). The enzymatic reaction was terminated after 30 minutes at 25° C. with 50 µl of 0.5 N NaOH, and the absorbance of each well measured at 405 nm. Though some inhibition of CD2 binding was observed, the PIC 024.4 IC$_{50}$ (71 µg/ml) was at least two orders of magnitude weaker than the effect on the gp120/CD4 ELISA (FIG. 11). Although IC$_{50}$ values obtained using different assay systems are not necessarily comparable, the formats used here are the same, and the avidities of the CD2-IgM/CD58 and gp120/CD4 interactions are estimated to be similar. These results thus suggest that PIC 024.4 selectively interferes with gp120/CD4 interaction.

2.1.8 Rosette Inhibition Assay: CD2/LFA-3 (CD58)

Sheep red blood cells (SRBC) (Whittaker-Bioproducts, Walkersville, Md.) were pretreated with 2-aminoethylisothiouronium bromide (AET, 40 µg/ml) for 15 minutes at 37° C., washed in HANK'S Balanced Salt Solution (HBSS Mediatech) +2.5% FCS, and resuspended to 1.5×10$^9$ cells/ml. Jurkat cells were washed in HBSS+2.5% FCS, and resuspended in the same at a concentration of 1.25×10$^7$ cells/ml. Twenty µl of Jurkat cells were incubated with 20 µl of PIC 024.4 at various concentrations (100, 40, 20 and 10 µg/ml based on total weight) for 30 minutes at 4° C. SRBC ($1.5 \times 10^7$ in 10 µl) were added to the Jurkat cells, and the cells were incubated together for 5 minutes at room temperature, centrifuged at 300 rpm for 5 minutes, then incubated on ice for 1 hour. Cells were gently resuspended, diluted with HBSS+2.5% FCS and observed in a hemacytometer. PIC 024.4 showed little to no inhibition in this assay.

2.1.9 Inhibition of gp120 Binding to Lymphocytes in Whole Blood

This assay was used to measure the ability of test compounds to inhibit the binding of recombinant gp120 to the CD4 receptor expressed on the surface of lymphocytes in whole blood. Freshly collected, anticoagulated whole blood from normal donors (100 µl per tube) was treated with test compound and incubated for 2 hours at room temperature. The tubes were then treated with gp120-biotin (American Bio-Technology Products) to a final concentration of 10 nM, and incubated for an additional 3 hours at room temperature. Cells were then stained with fluorescein-labeled streptavidin (Becton Dickinson), treated with lysis buffer (Becton Dickinson), and washed with PBS containing 0.1% azide. Cells were then subjected to flow cytometric analysis on a FACScan™ flow cytometer (Becton Dickinson) and the mean fluorescence for the lymphocyte population was measured. Percent inhibition of fluorescence was determined relative to cells that were not treated with drug.

All of the PRO 2000 fractions inhibited gp120 binding to lymphocytes with $IC_{50}$'s ranging from 11 to 151 µg/ml (FIG. 15). By contrast, dextran sulfate (8 kD) showed little or no inhibition ($IC_{50} \geq 1000$ µg/ml).

The octamer (PRO 1191) and hexamer (PRO 1073) inhibited binding with $IC_{50}$'s of 130 and 600 µg/ml, respectively (FIG. 15B).

2.1.10 Inhibition of gp120 Binding to CD4 on a Biosensor Surface

This assay provided a direct measure of the ability of test compounds to inhibit the gp120/CD4 binding interaction. The BIAcore™ biosensor (Pharmacia Biosensor) allows for real-time interaction analysis without the need for labeling (Jonsson et al., *BioTechniques* 11:620–627 (1991); Malmquist, *Nature* 361:186–198 (1993)). Its operation is based on optical surface plasmon resonance (SPR) for detecting small changes in the refractive index on the surface of a thin gold film coated with a dextran matrix to which one ligand is immobilized. In the experiments described here, recombinant sCD4 was immobilized to the sensor surface by a standard amine coupling chemistry. Recombinant gp120 (SF2 isolate), alone or in the presence of test compound, was passed over the surface, and binding monitored by a change in "resonance units" (RU's). Percent inhibition was determined relative to RU levels observed in the absence of drug. A correction was made to account for the mass of the test article.

The binding of gp120 was inhibited in a dose-dependent manner by each of the PRO 2000 fractions (FIG. 16). The $IC_{50}$'s for PRO 2000/5, PRO 2000/10 and PRO 2000/25 were similar (~10 µg/ml), while the $IC_{50}$ for PRO 2000/3 was slightly higher (22 µg/ml). Dextran sulfate (8 kD) was inactive in the assay.

2.1.11 Inhibition of Monoclonal Antibody Binding to CD4

A panel of related ELISA systems was used to evaluate the effect of test compounds on the binding of various monoclonal antibodies to recombinant sCD4 absorbed on plastic. Two of these antibodies, Leu3A and 19Thy, are directed against gp120 binding site on CD4. A third, OKT4, does not block gp120 binding. The ELISA formats were similar to those used to measure gp120 binding to CD4. Plates coated with recombinant, soluble CD4 were treated with antibody (30 ng/ml) and serial dilutions of drug. After incubation and washing, bound antibody was detected using an appropriate isotype-specific anti-immunoglobulin alkaline phosphatase conjugate.

All four PRO 2000 fractions inhibited the binding of 19thy and Leu3A, but did not affect the binding of OKT4 (FIG. 17A–17C). The $IC_{50}$'s again showed a slight dependence on molecular weight. Aurintricarboxylic acid also inhibited the binding of Leu3A and 19Thy ($IC_{50}$'s of 124 and 87 µg/ml, respectively) but, like the fractions, did not affect the binding of OKT4. These results suggest that PRO 2000 binds specifically to the gp120 binding site on CD4. The $IC_{50}$ values may be higher (i.e. less potent) than in the gp120/CD4 ELISA due to the higher binding avidity of the antibodies.

2.2 Antiviral Activity 2.2.1 Antiviral Activity and Cytotoxicity Assay of CEM Cells Employing HTLV-IIIB:

PIC 024.4 (30% by wt. naphthalene sulfonic acid condensate) was dissolved in sterile water at a concentration of 4 mg/ml. Dilutions were prepared in culture medium, and the compound was tested at concentrations ranging from 100 µg/ml to 0.003 µg/ml in half-$\log_{10}$ dilutions.

The assay was done in 96-well tissue culture plates using the CEM-T4 human T-lymphocyte cell line. The culture medium used was RPMI-1640 medium containing 25 mM N-[2-Hydroxyethyl]piperazine-n$^1$-[2-ethanesulfonic acid] (HEPES, Sigma Chemical Co.) and 2 mM L-glutamine, and supplemented with 10% fetal bovine serum, 2 mM L-glutamine, 50 units of penicillin G per ml, and 50 µg streptomycin sulfate per ml. CEM-T4 cells were treated with polybrene at a concentration of 2 µg/ml, and a 130 µl volume of cells ($1 \times 10^4$ cells) was dispensed into each well. To one assay plate for each drug a 50 µl volume of each drug dilution (prepared as a 4×concentration) was added to five wells of cells, and the cells were incubated at 37° C. for two hours. This resulted in the pre-treatment of the cells with drugs at a 1.1×concentration. A second assay plate for each drug, containing just the dispensed cells, was incubated in parallel.

For all assay plates, a frozen culture of HIV-1, strain HTLV-III$_B$, was diluted in culture medium to a concentration of $2.5 \times 10^4$ TCID$_{50}$ per ml, and a 20 µl volume (containing 500 TCID$_{50}$ of virus) was added to three wells for each drug concentration. This resulted in a multiplicity of infection of 0.05 for the HIV-1 infected samples. A 20 µl volume of normal culture medium was added to two wells for each drug concentration to allow evaluation of drug cytotoxicity.

After a two hour incubation with virus at 37° C., a 50-µl volume of each drug dilution (prepared as a 4×concentration) was added to three infected wells of cells and to two uninfected wells of cells for the second assay plate of each drug.

Each assay plate contained five wells of untreated, uninfected, cell control samples and five wells of untreated, infected, virus control samples. 2',3'-Dideoxyinosine (DDI) was assayed in parallel using both protocols for drug addition.

The tissue culture plates were incubated at 37° C. in a humidified, 5% CO$_2$ atmosphere and observed microscopically for toxicity and/or cytopathogenic effect. On the eighth day post-infection, the cells in each well were suspended and a 50-µl sample of each cell suspension was transferred to a new 96-well plate for use in the following assay. A 100-µl volume of fresh RPMI-1640 medium and a 30-µl volume of a 5-mg/ml solution of 3-(4,5-dimethylthiazol-2-yl)-2,5- diphenyltetrazolium bromide (MTT) were added to each 50-μl cell suspension, and the cells were incubated at 37° C. in 5% $CO_2$ for four hours. During this incubation MTT is metabolically reduced by living cells, resulting in the production of a colored formazan product. A 50-μl volume of a solution of 20% sodium dodecyl sulfate in 0.02 N hydrochloric acid was added to each sample, and the samples were incubated overnight. The absorbance at 590 nm was determined for each sample using a Molecular Devices $V_{max}$ microplate reader. This assay detects drug-induced suppression of viral cytopathic effect (CPE), as well as drug cytotoxicity, by measuring the generation of MTT-formazan by surviving cells. When a dose-dependent effect for either CPE-inhibition or toxicity was seen, values for the 50% effective dose were calculated using the dose-effect analysis software of Chou and Chou (Elsevier-Biosoft).

The results are summarized in Table 5.

2.2.2 In Vitro Anti-HIV Assay and Cytotoxicity Assay Employing Strain JR-CSF:

The purpose of this procedure is to look at the toxicity and effect of a compound on free HIV virus infection of human phytohemagglutinin (PHA) blasts, in vitro, for a virus isolate (JR-CSF) which has previously been shown to be resistant to therapy with recombinant soluble CD4 (sCD4). The day before setting up an assay, human PHA activated T cell blasts were thawed from liquid nitrogen and cultured overnight in Iscove's Modified Dulbecco Medium (IMDM) plus 7% FCS and 50 units/ml IL-2 at a density of $10^6$/ml.

PHA activated T cell blasts were pelleted and resuspended at $4\times10^6$ per ml in medium containing 7% FCS and 50 units/ml IL-2. Twenty-five μl of the cell suspension were plated per well in round bottom 96-well microtiter plates ($10^5$/well) and placed in a 37° C. incubator. Twenty-five μl of the compound to be tested at appropriate dilutions in 7% FCS/IMDM containing 50 units/ml IL-2 (2×the final concentration) or tissue culture medium alone (as a negative control) were added to the cells and incubated for 2 hours at 37° C. Two hundred μl of medium was added and the test compound was washed out by centrifugation of the 96 well plates for 2 minutes at 1000 rpm and aspiration of 250 μl. The cells were resuspended in 50 μl medium containing 7% FCS and 50 units/ml IL-2. HIV-1 (JR-CSF, Koyanagi et al., Science, 236:819–821 (1987)) was diluted to 50 $TCID_{50}$ (in 25 μl) in IMDM containing 7% FCS and 50 units/ml IL-2 plus polybrene (10 μg/ml) in 24 well plates. Twenty-five μl of virus were added per well to the cells. HIV infection was allowed to proceed for 2 hours at 37° C., followed by addition of 200 μl of medium. The virus was washed out by centrifugation of the 96 well plates for 2 minutes at 1000 rpm, aspiration of 250 μl, and addition of 200 μl of fresh medium containing 7% FCS and 50 units/ml IL-2 and the appropriate amount of test compound (1×). Medium was removed and replaced with fresh medium containing 7% FCS and 50 units/ml IL-2 plus test compound (1×) on day 4. On day 7, the plates were centrifuged at 1000 rpm for 5 minutes, and supernatants were carefully removed from each well. The cells were lysed and assayed for p24 antigen at a 1:35 dilution.

Percent inhibition was determined relative to untreated, infected control cells. For instance, if the amount of p24 antigen in control well is A and the amount of p24 in a well with a test compound is B, then the compound achieves (A-B/A)(100) % inhibition of that concentration.

In establishing toxicity, PHA activated T cell blasts were pelleted and resuspended at $2\times10^6$ per ml and plated in 96 well round bottom microtiter plates at $10^5$ per well (50 μl) in IMDM plus 7% FCS and 50 units/ml IL-2. Twenty-five μl of the compound to be tested at appropriate dilutions in 7% FCS/IMDM containing 50 units/ml IL-2 (3×the final concentration) or tissue culture media alone (controls) was added to the 96 well plate. This mixture was incubated for 2 hours at 37° C., followed by addition of 200 μl of medium. The test compound was washed out by centrifugation of the 96 well plate(s) for 2 minutes at 1000 rpm, aspiration of 250 μl, and addition of 200 μl of fresh medium containing IL-2 and the appropriate amount of test compound (1×). Medium was removed and replaced with fresh medium containing test compound on day 4.

At day 7, the appropriate number of cells (100 μl) was transferred to another plate. Toxicity of the test compounds was assayed by the MTT assay, substantially as described above.

Analysis of AZT indicated no cytotoxicity in the concentration range of 0.0004–50 μM. p24 levels were substantially reduced in the anti-HIV assay using JR-CSF at concentrations of 0.004–50 μM where the drug was added 2 hours prior to infection. Anti-HIV activity was clearly demonstrated for this compound. The results achieved were in the range of expected values obtained from previous assays.

Analysis of PIC 024.4 indicated slight cytotoxicity at only the highest concentration tested: 100 μg/ml. p24 levels were substantially reduced in the anti-HIV assay using JR-CSF and concentrations of PIC 024.4 equal to 100, 20, and 4 μg/ml where the drug was added 2 hours prior to infection. Anti-HIV activity was clearly demonstrated for this compound with activity observed at a concentration 25-fold below that where toxicity was observed.

Figure 2:
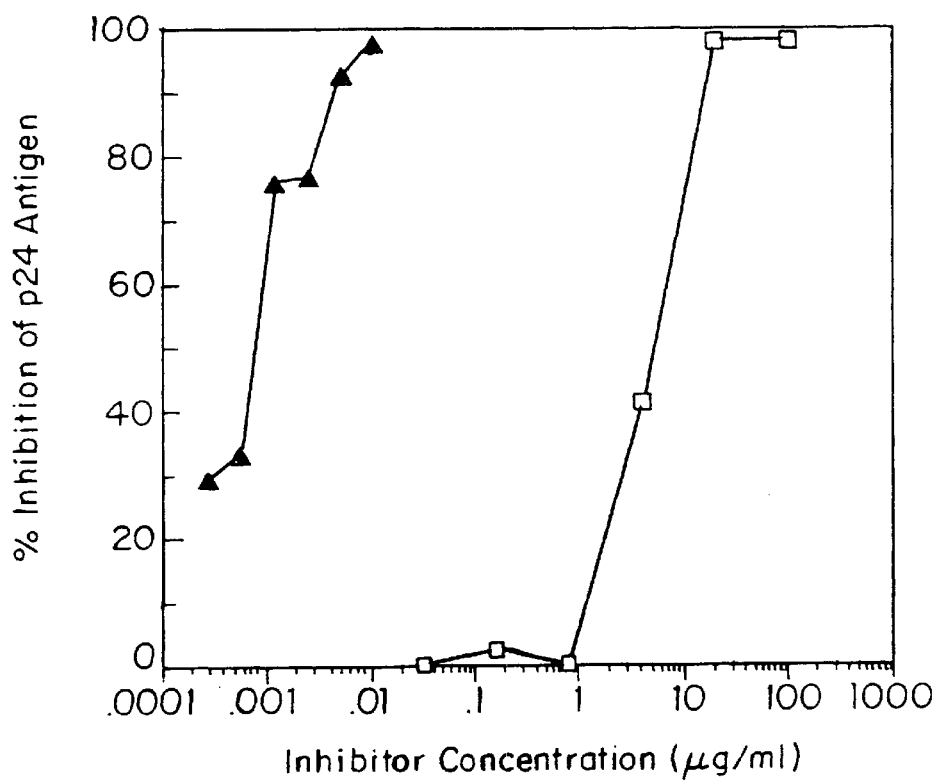
FIG. 2 is a graph of an in vitro anti-HIV activity of PIC 024.4 (30% NSA, designated by an open square) and AZT (designated by a closed triangle) against HIV (strain JR-CSF).

The results are summarized in Table 5 and illustrated in FIG. 2.

2.2.3 Human Monocyte-Macrophage Studies with HIV-1 (ADA): Assays of HIV Infection of Monocyte Targets Human peripheral blood leukocytes were obtained by countercurrent centrifugal elutriation and the monocytes allowed to adhere to the surface of tissue culture flasks. The monocytes were cultured as an adherent monolayer for 7-days in DMEM supplemented with 10% heat-inactivated human $AB^+$ serum, 50 μg/ml gentamycin, and 1,000 units/ml macrophage colony stimulating factor (mCSF, Cetus). Pre-incubation in mCSF was performed because it markedly increases (7 to 10 fold) HIV-1 expression in vitro. After pre-incubation, the cell population harvested by scraping was shown to contain >98% monocytes using cell morphology on Wright-stained cytosmears, and histochemical staining for granular peroxidase and nonspecific esterase. The monocytes at a concentration of $1\times10^6$/ml were then added to the wells of 24-well plates and allowed to form adherent monolayers. Prior to infection with HIV-1, the media was aspirated carefully from each well. The plates were washed carefully three times with 37° C. PBS to remove all residual serum. Thirty to fifty μl/well of $HIV_{ADA}$ strain (D. Chester Kalter et al., J. Immunol. J46:298–306 (1992)) in 70–50 μl RPMI (this represents 3.0 $\log_{10} TCID_{50}/10^5$ cells) was added, and incubated for at least 2 hours at 37° C. Compounds were added in 10% FCS RPMI with mCSF (C-34) at 1,000 units/ml to the plates. Controls included: +cells +virus; +cells −virus; and −cells +virus. On day 7, the supernatant was removed as follows: 1 ml for reverse transcriptase, 0.5 ml for p24 assay, and the medium was replenished with fresh drug. The final harvest was on day 14.

Figure 3:
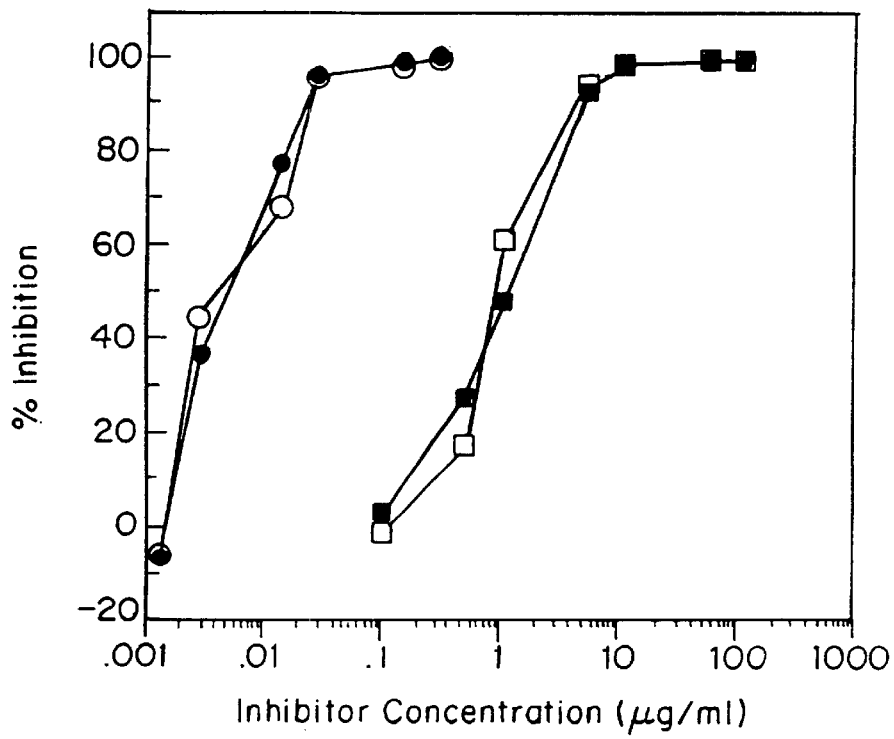
FIG. 3 is a graph of in vitro anti-HIV (strain ADA) activities at Days 7 and 14 of PIC 024.4 (30% NSA, designated by an open square at Day 7 and a closed square at Day 14) and AZT (designated by a open circle at Day 7 and a closed circle at Day 14).
Figure 4:
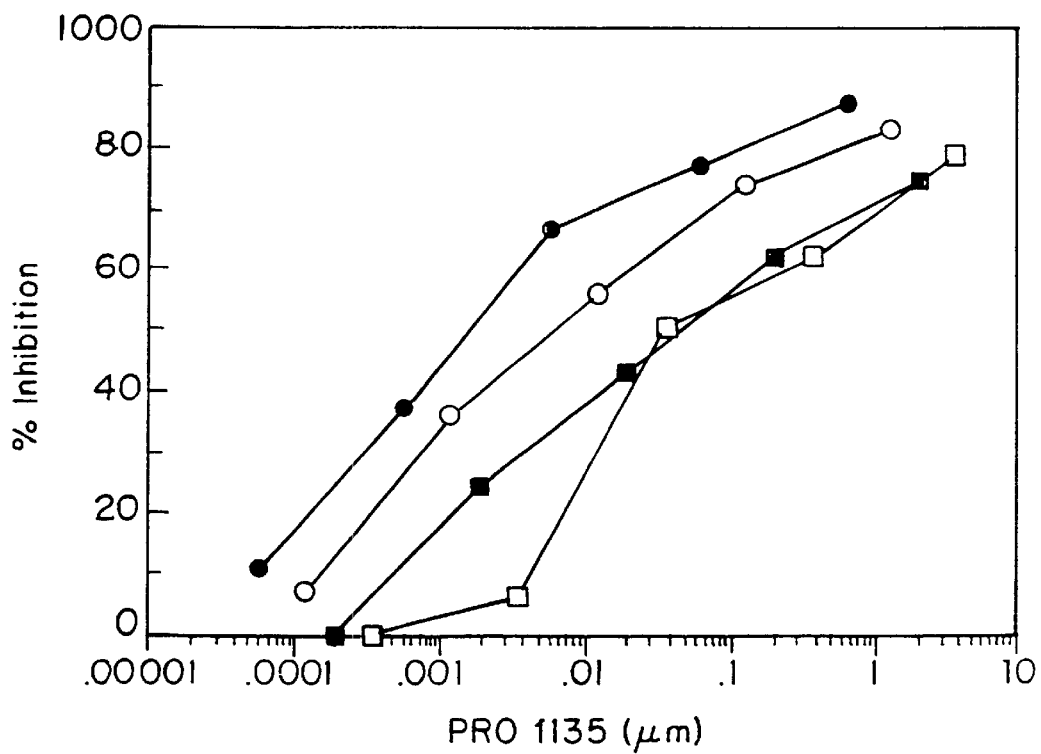
FIG. 4 is a graphic illustration of the size/activity relationship of fractions of PRO 1135 possessing a peak molecular weight of 5.6 kDa (open square), 10 kDa (closed square), 16 kDa (open circle) and 31 kDa (closed circle) in the inhibition of gp120 binding to sCD4 (ELISA).
Figure 5:
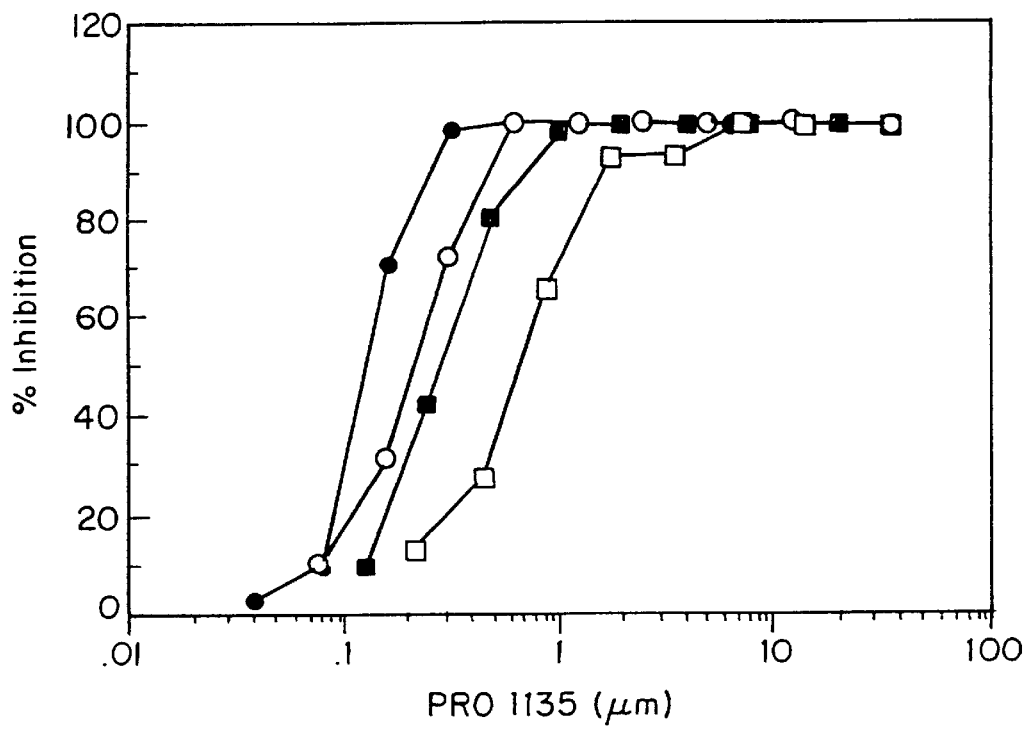
FIG. 5 is a graph of the size/activity relationship of fractions of PRO 1135 possessing a peak molecular weight of 5.6 kDa (open square), 10 kDa (closed square), 16 kDa (open circle) and 31 kDa (closed circle) in the inhibition of gp120 binding in the CD4/gp120, binding assay: cellular.
Figure 6:
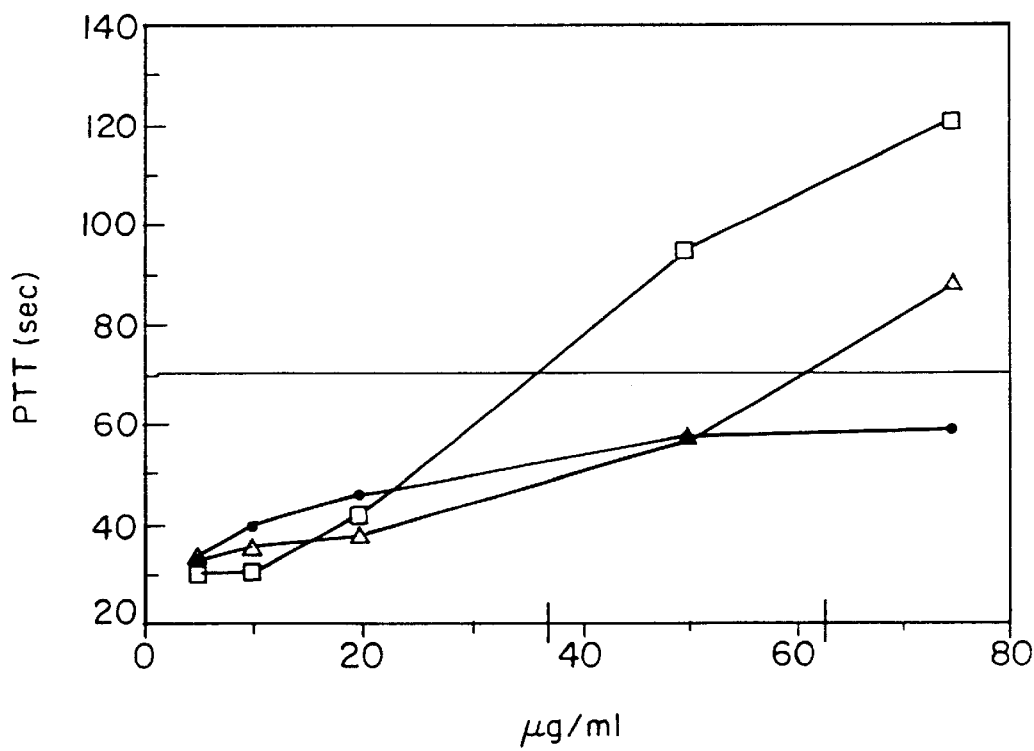
FIG. 6 is a graphic illustration of the anticoagulation activity of the 31 kDa (open square), 10 kDa (closed square) and 5.6 kDa (closed diamond) fraction of PRO 1135.
Figure 8:
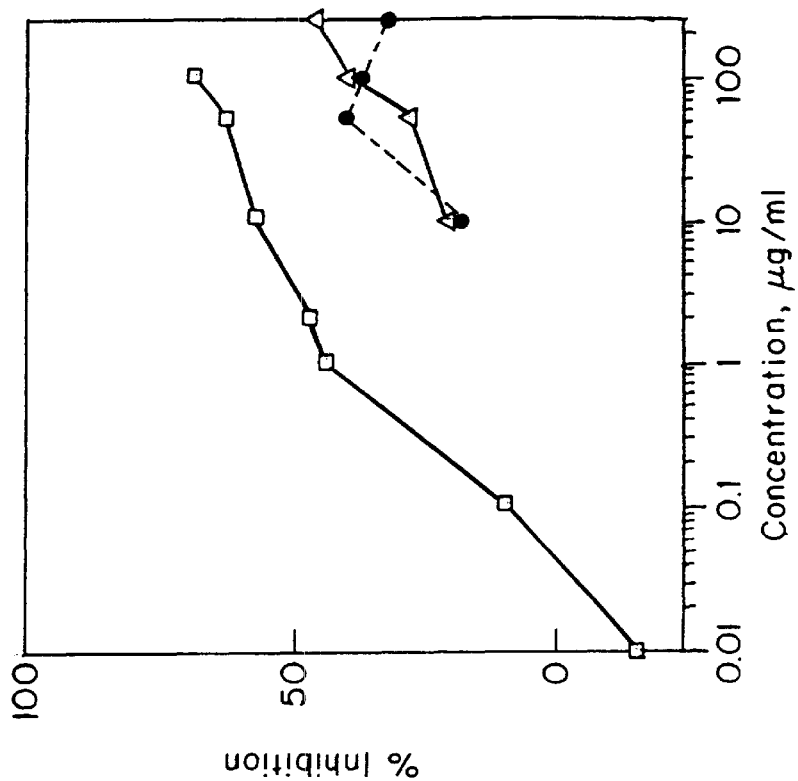
FIG. 8 is a graphic illustration of the ELISA assay for inhibition of CD4-gp120 binding for PRO 1191 (octamer, open square), PRO 1072 (tetramer, open diamond) and PRO 1073 (hexamer, open circle) of the formaldehyde-2-naphthalenesulfonic acid condensate oligomer.
Figure 7:
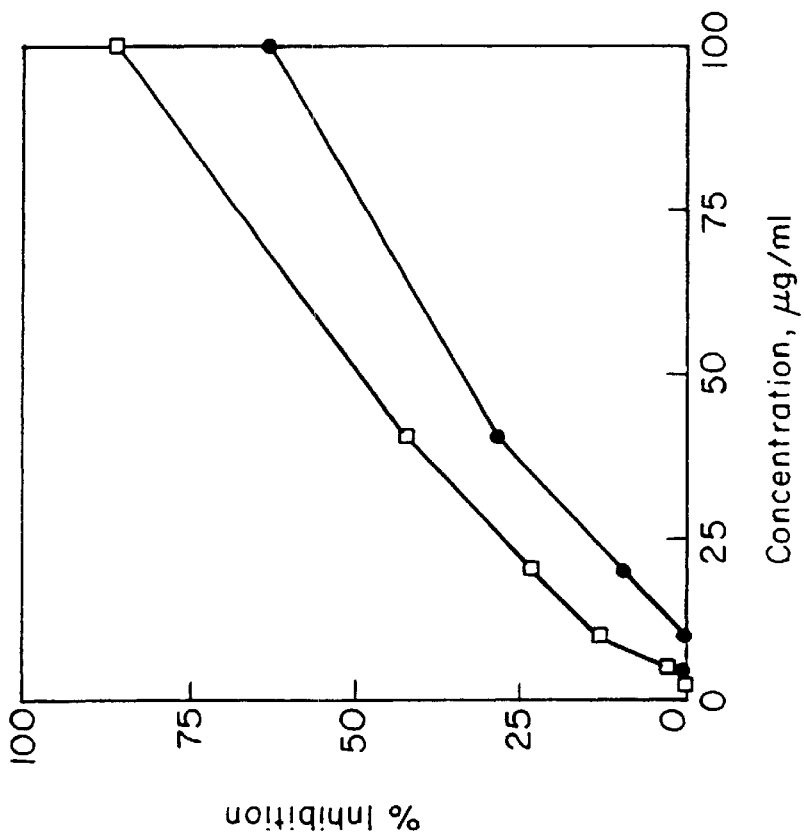
FIG. 7 is a graphic illustration of the inhibition of gp120 binding to CD4 in the cellular assay for PRO 1191 (octamer, open square) and PRO 1072 (tetramer, open diamond) of the formaldehyde-2-naphthalenesulfonic acid condensate oligomer. PRO 1191 and PRO 1072 exhibited an $IC_{50}$ of 52 and 78, respectively.

The results are summarized in Tables 5 and 6 and illustrated in FIG. 3.

TABLE 5

| Compound | Antiviral Activity $ID_{50}$ (μg/ml) | | | Cytotoxicity $TD_{50}$ (μg/ml) | |
|---|---|---|---|---|---|
| | $III_B$ | JR-CSF | ADA | CEM-T4 ($III_B$) | T-Blasts (JR-CSF,ADA) |
| PIC 024.4** | 8.4 | ≈4 | 1.0 | >100 | >100 |
| ddI | 1.2 | | | >25 | |
| AZT | | 0.001 | 0.005 | | >10 |
| Dextran Sulfate* | | | | | |
| AHT 8 | 8 | | | | |
| TM 11 | 4 | | | | |

*(Science, 240:646–649, 1988)
**(30% polymer by weight)

TABLE 6

| Drug | EC50 (μg/ml) | | EC90 (μg/ml) | |
|---|---|---|---|---|
| | Day 7 | Day 14 | Day 7 | Day 14 |
| PIC 024.4 | 1.02 | 0.93 | 3.17 | 3.48 |
| AZT | 0.005 | 0.003 | 0.02 | 0.01 |

2.2.4 Inhibition of the Infection of H9 Cells by HIV-1 IIIB

This assay was used to assess the effect of test compounds on the growth of HIV-1 IIIB on cells of the H9 human T-lymphoblastoid line. The toxicity of drug toward uninfected H9 cells was also determined. In the assay, H9 cells were cultured in RPMI 1640 medium containing 10% FBS, 50 units/ml penicillin, 50 μg/ml streptomycin, 2 mM L-glutamine, and 10 mM HEPES buffer. Cells were transferred to 24-well plates ($0.75 \times 10^6$ cells/well) and treated, at the same time, with various concentrations of test compound and 500 $TCID_{50}/10^6$ cells of cell-free HIV-1 IIIB. Recombinant, sCD4 was tested in parallel. Cultures were incubated at 37° C. in a humidified, 5% $CO_2$ atmosphere. In some experiments, cells were washed after one or three days to remove drug. On day 4, cells were passaged at a 1:4 ratio to fresh medium. On days 7 and 11, culture supernatants were tested for p24 activity and cell counts were performed. Percent inhibition of p24 production was calculated relative to untreated, infected cells. To assess cytotoxicity, various dilutions of test compound were incubated with uninfected cells. Cells were passaged to fresh medium on day 4, and viability was assessed on days 7 and 11 by trypan blue exclusion. Percent survival was calculated relative to untreated, uninfected cells.

2.2.5 Inhibition of the Infection of Human PBL Blasts by HIV-1 14aPre and N70

These assays were used to assess the effect of test compounds on the growth of the lymphotropic clinical isolates 14aPre and N70 on PHA-activated human PBL's. Isolate 14aPre was derived from an HIV-positive individual who had not received antiretroviral therapy (Johnson, V. A. et al., *J. Infect. Dis.* 164:646–655 (1991)). Isolate N70 was obtained from an asymptomatic patient (Conner, R. I. et al., *AIDS Res. Hum. Retroviruses* 9:541–546 (1993)). In the assays, 3-day PHA-activated human PBMC's were cultured in RPMI 1640 medium containing 20% FBS, 50 units/ml penicillin, 50 μg/ml streptomycin, 2 mM L-glutamine, 10 mM HEPES buffer, and 10% IL-2. In a 24-well plate, cells ($1.5 \times 10^6$ per well) were treated with multiple dilutions of either single drug or combinations of test compound and either AZT, DDI, or sCD4. At the same time, virus (1000 $TCID_{50}/10^6$ cells) was added and the cultures incubated at 37° C. in a humidified, 5% $CO_2$ atmosphere. On day 4, cells were resuspended and passaged at a 1:3 ratio to fresh medium containing drug. On days 4 and 7, culture supernatants were tested for p24 activity and cell counts were performed.

2.2.6 Inhibition of the Infection of Fresh Human Macrophages by HIV-1 Ba-L

This assay was used to assess the effect of test compounds on the growth of the monocytotropic laboratory-adapted isolate HIV-1 Ba-L (Gartner, S. et al., *Science* 233:215–219 (1986)) on fresh, elutriated human macrophages. Uninfected GM-CSF-stimulated monocytes/macrophages ($\sim 0.3 \times 10^6$) were treated with 1 ml of RPMI 1640 medium supplemented with 10% FBS, 50 units/ml penicillin, 50 μg/ml streptomycin, 2 mM L-glutamine, and 10 mM HEPES buffer (R-10 medium), as well as test compound or control drugs. After two hours incubation, cells were treated with a cell-free stock of HIV-1 Ba-L (5 ng/ml p24 equivalent). After one day, cells were washed and 1 ml of R-10 medium containing the original concentration of test compound. Cultures were incubated at 37° C. in a humidified, 5% $CO_2$ atmosphere. On day 7, culture supernatants were tested for p24 activity and cell counts were performed. Percent inhibition of p24 production was calculated relative to untreated, infected cells.

Results (2.2.4; 2.2.5; 2.2.6)

PIC 024.4 was shown to inhibit infection by HIV-1 IIIB, two clinical isolates (14aPre and N70), and the monocytotropic isolate Ba-L with $IC_{50}$'s comparable to those observed in the previous experiments (Tables 5 and 7). In some experiments, PIC 024.4 was cytotoxic at high concentration. Independent studies showed that this toxicity was observed only occasionally, and that it seemed to depend on the handling of the cells prior to drug treatment. When present, the toxicity appeared only after four days in culture. Recent experiments have shown that PIC 024.4 can suppress viral growth when removed from culture after an incubation period of one to three days. No cytotoxicity was observed under these conditions.

PRO 2000/5 was assayed for the ability to suppress the growth of HIV-1 IIIB on cultured H9 cells. Infectious virus and serial dilutions of PRO 2000/5 were added to the cultures on day 0, and on day 3 the cells were washed and resuspended in either drug-free medium or medium containing 1 μg/ml PRO 2000/5. Viral growth was assessed by measurement of p24 antigen on day 11. Under both sets of conditions, PRO 2000/5 inhibited viral growth with an $IC_{50}$ of 4–5 μg/ml, and no cytotoxicity was observed (FIG. 20).

2.2.7 Inhibition of the Infection of CEM-SS Cells by HIV-1 IIIB

This assay was used to measure the effect of test compound on the survival of CEM-SS cells following infection by HIV-1 IIIB. In a 96-well microtiter plate, CEM-SS cells in RPMI-1640 medium supplemented with 10% fetal bovine serum, gentamycin, and antibiotics ($2.5 \times 10^4$ cells/ml, 50 μl/well) were treated with serial dilutions of test compound or the antiviral agents AZT or dideoxycytidine (DDC). Cells were incubated for two hours at 37° C. and then treated with cell-free HIV-1 IIIB at a multiplicity of infection (MOI) of 0.05. Identical drug-containing wells were left uninfected to assess cytotoxicity. The plates were then incubated at 37° C. in a humidified, 5% $CO_2$ atmosphere. On day 6, an aliquot of cells from each well was incubated with the tetrazolium dye XTT (2,3-bis[2-methoxy-4-nitro-5-sulfenyl]-2H-tetrazolium-5-carboxanilide) at 37° C. for four hours, and the colored formazan product quantitated by measuring the absorbance of each sample at 450 nm. These values were used to calculate percent survival and percent inhibition of virus-induced cytopathic effect (CPE) at each drug concentration.

Each of the PRO 2000 fractions inhibited the infection of CEM-SS cells by HIV-1 IIIB with an $IC_{50}$ of ~2 µg/ml (FIG. 18). The inhibitory activities showed little dependence on molecular weight, though PRO 2000/3 appeared to be slightly less potent than the three larger fractions.

2.2.8 Inhibition of Infection by Single-passage HIV-1 Isolates

Compounds were tested for their ability to inhibit infection by a panel of single-passage "clinical isolates." Each of the isolates was obtained by standard co-culture techniques from the peripheral blood cells of pediatric patients being treated at the University of Alabama at Birmingham Children's hospital. Each of the isolates was grown only in PBMC's. Viral phenotypes are shown in Table 7. The amount of each virus used in the assays was determined by the amount of virus required to give peak p24 or reverse transcriptase activity in tissue culture supernatants at day 7 post-infection.

Isolates WEJO, BAKI, and VIHU were grown on activated human PBL's. Fresh PBMC's obtained from HIV-seronegative donors were isolated by Ficoll-Hypaque density centrifugation, suspended in RPMI 1640 medium supplemented with 2 mM L-glutamine, 50 µg/ml gentamicin, and 15% FBS ($1 \times 10^7$ viable cells/ml) and treated with PHA (3 µg/ml) at 37° C. for 38–72 hours. Activated PBL's were then infected with cell-free virus stock at an MOI yielding a satisfactory p24 ELISA value (or reverse transcriptase activity) seven days post infection. Infected cells were then suspended in medium containing recombinant human IL-2 (30 U/ml) and plated on a 96-well microtiter plate ($4 \times 10^4$ cells/well) containing serial dilutions of test compound or control solution. Seven days post-infection, culture supernatants were tested for p24 or reverse transcriptase activity, and cell viability was assessed by the trypan blue exclusion method.

Isolate SLKA was grown on fresh human macrophages. Fresh PBMC's were plated in a 96-well plate at a density of $3 \times 10^6$ cells/ml in HBSS with calcium and magnesium supplemented with 10% heat-inactivated human AB serum. Plates were incubated at 37° C. in a humidified atmosphere of 5% $CO_2$ for 2 hours. The monolayer of adherent macrophages was washed 6 times with HBSS (with calcium and magnesium) to remove nonadherent cells, and the monolayer was then incubated in RPMI 1640 medium supplemented with 15% FBS, antibiotics, and L-glutamine. After 7 days of incubation the monolayer was washed 6 times to remove any nonadherent cells and protein bound to the cell surface, and treated with serial dilutions of test compound or control drug. Virus was added to the appropriate wells and the plate incubated for 4 hours at 37° C., after which the plate was washed to remove excess virus. Wells were then treated with medium alone or medium containing drug, and incubated for 7 days at 37° C. in a humidified 5% $CO_2$ atmosphere. Culture supernatants were then assayed for p24 activity, PRO 2000/5 was tested for activity against three lymphotropic primary clinical isolates (Table 7). These isolates were obtained from pediatric AIDS patients, and represent syncytium-inducing and nonsyncytium-inducing phenotypes. Recombinant sCD4 was inactive against all three isolates (up to a concentration of 50 µg/ml). PRO 2000/5 inhibited infection by all of these isolates with an $IC_{50}$ of 1–2 µg/ml (FIG. 19). The compound also inhibited the infection of macrophages by the primary monocytotropic isolate SLKA with an $IC_{50}$ of 6.1 µg/ml. Dextran sulfate has been reported to be inactive against many monocytotropic isolates (Meylan, P. R. A. et al., Antimicrob. Agents Chemother. 38:2910–2916 (1994)).

The octamer (PRO 1191), hexamer (PRO 1073) and tetramer (PRO 1072) inhibited infection with $IC_{50}$'s of 25, 28 and 78 µg/ml, respectively (FIG. 19B).

2.2.9 Inhibition of gp120-mediated Syncytium Formation

Cells expressing the HIV-1 envelope protein on their surface can fuse with cells expressing the CD4 receptor to form giant, multinucleated cells called "syncytia". The effect of test compound on syncytium formation was evaluated using an assay developed by Dr. George Pavlakis and coworkers (Ciminale, V. et al., AIDS Res. Hum. Retroviruses 6:1281–1287 (1990)). Cells of the HeLa-CD4-LTR-β-gal line (a HeLa line transfected with the CD4 and Escherichia coli β-galactosidase genes, the latter under control of the HIV-1 LTR promoter) were transferred to a 96-well microtiter plate ($5 \times 10^3$ cells/well) and treated with serial dilutions of test compound for 1 hour. The wells were then treated with $5 \times 10^3$ cells of the HL2/3 line (a HeLa line transfected with an HIV-1 HXB2 provirus, which expresses the viral envelope and tat proteins but does not produce infectious viral particles). The cultures were then incubated in the presence of drug for 48 hours at 37° C., fixed and stained with X-gal. Blue syncytia were counted using an inverted microscope, and percent inhibition and $IC_{50}$ values were calculated.

PIC 024.4 was shown to inhibit syncytium formation by two transfected HeLa cell lines with an $IC_{50}$ of 1.2 µg/ml (FIG. 21). The inhibition curve was similar to those obtained in the neutralization assays, confirming that the antiviral activity of the PRO 2000 series is due to an effect on the initial steps of HIV-1 infection. As expected, AZT was inactive in the syncytium inhibition assay, though dextran sulfate (8 kD) gave an $IC_{50}$ of 0.9 µg/ml.

Each of the PRO 2000 fractions inhibited syncytium formation in the HL2/3 assay (FIG. 22). Again, the $IC_{50}$ values were remarkably consistent, ranging from 0.4 to 0.7 µg/ml.

The octamer (PRO 1191), hexamer (PRO 1073), tetramer (PRO 1072) and dimer (PRO 1055) showed somewhat lower activities, with $IC_{50}$'s ranging from 6 to 60 µg/ml (FIG. 22B).

TABLE 7

PRO 2000 and PIC 024.4 ANTIVIRAL ACTIVITY SUMMARY

| | | | | $EC_{50}$ (µg/ml) | |
|---|---|---|---|---|---|
| HIV Isolate | Tropism | Phenotype | Target Cell | PIC 024.4* | PRO 2000 |
| Laboratory Isolates | | | | | |
| IIIB | Lymphocytes | SI | CEM | 2.5 | |
| IIIB | | | H9 | 0.51 | |
| IIIB | | | CEM-SS | | 1.7 |
| RF | Lymphocytes | SI | CEM-SS | | 3.5 |
| ADA | Monocytes | | Macrophages | 0.30 | |
| BaL | Monocytes | SI | Macrophages | 1.2 | |
| Clinical Isolates | | | | | |
| JR-CSF | Lymphocytes | NSI | PBL's | 1.5 | |
| 14aPre | Lymphocytes | NSI | PBL's | 10 | |
| N70 | Lymphocytes | NSI | PBL's | 4.0 | |

TABLE 7-continued

PRO 2000 and PIC 024.4 ANTIVIRAL ACTIVITY SUMMARY

| | | | | EC$_{50}$ ($\mu$g/ml) | |
|---|---|---|---|---|---|
| HIV Isolate | Tropism | Phenotype | Target Cell | PIC 024.4* | PRO 2000 |
| Primary Isolates | | | | | |
| WEJO | Lymphocytes | SI | PBL's | | 0.9 |
| BAKI | Lymphocytes | SI | PBL's | | 1.6 |
| VIHU | Lymphocytes | NSI | PBL's | | 2.1 |
| SLKA | Monocytes | NSI | Macrophages | | 6.1 |
| Syncytium Inhibition | | | | | |
| HL 2/3 env+ Cells | | | HeLa-CD4-LTR-β-gal Cells | 1.2 | 0.6 |

*based on 100% polymer by weight 2.2.10 Evaluation of Long-term Cultures for Development of Resistance Isolate 14aPre was used to assess the development of resistance to the prototype preparation PIC 024.4. PBMCs from a normal, uninfected donor were suspended in RPMI 1640 medium containing 20% FBS, 50 units/ml penicillin, 50 μg/ml streptomycin, 2 mM L-glutamine, 10 mM HEPES buffer, and 10% IL-2. Cultures were infected with HIV-1 14aPre (1000 TCID$_{50}$/10$^6$ cells) and incubated at 37° C. in humidified, 5% CO$_2$ atmosphere. PIC 024.4 was added to the culture medium and its concentration was gradually increased over time (in increments of 3 μg/ml every 4 weeks) from 3 to 12 μg/ml. Cells were passaged onto fresh drug-containing medium at a 1:2 ratio and p24 antigen production was assayed two times per week; fresh PBMC were added once per week. Virus was isolated from the culture at days 91 and 212, and the ability of PIC 024.4 to neutralize these isolates was assessed by the methods described above.

The IC$_{50}$'s for neutralization of the day-91 isolate and the day-212 isolate were equivalent to the IC$_{50}$ for the day-0 virus (10–12 μg/ml).

2.2.11 Drug Combination Studies

Because AIDS patients may receive a PIC 024.4-based drug in combination with other antiretroviral agents, the potential for synergy with AZT, DDI, and sCD4 was evaluated. Different concentrations of each drug individually or in combination were assayed for the ability to neutralize of HIV-1 14aPre, a virus isolated from an infected patient before the initiation of antiretroviral therapy. Drug interactions were evaluated by the median effect principle and the isobologram technique (Chou et al., Adv. Enzyme Regul. 22:27–55 (1981)), which was used to calculate a combination index CI for each interaction. CI values of <1, =1, and >1 indicate synergism, additive effects, or antagonism, respectively. The results (Table 8) suggest that PIC 0.24.4 acts synergistically with AZT and sCD4, and additively with DDI.

TABLE 8

| | PIC 024.4 (μg/ml) | | | | |
|---|---|---|---|---|---|
| AZT (μM) | 0 | 6 | 12 | 18 | 24 |
| 0 | 38 | 31.5 | 18.5 | 1.9 | 0.4 |
| 0.0025 | 35 | 23.5 [0.970] | | | |
| 0.005 | 25 | | 5.8 [1.048] | | |
| 0.01 | 17.5 | | | 0.5 [0.692] | |
| 0.02 | 9.8 | | | | 0.2 [0.726] |
| DDI (μM) | 0 | 6 | 12 | 18 | 24 |
| 0 | 38 | 31.5 | 18.5 | 1.9 | 0.4 |
| 1.25 | 36.5 | 17.5 [0.868] | | | |
| 2.5 | 21.5 | | 2.4 [1.003] | | |
| 5 | 11.2 | | | 0.3 [0.930] | |
| 10 | 1.2 | | | | 0.2 [1.314] |
| | PIC 0.24.4 (μg/ml) | | | | |
| sCD4 (μg/ml) | 0 | 6 | 12 | 18 | 24 |
| 0 | 38 | 31.5 | 18.5 | 1.9 | 0.4 |
| 40 | 34.5 | 25 [1.108] | | | |
| 60 | 27.3 | | 4.6 [0.977] | | |
| 80 | 27.1 | | | 0.4 [0.627] | |
| 100 | 22.8 | | | | 0.3 [0.637] |

3. TOXICITY AND T CELL PROLIFERATION STUDIES 3.1 T Cell Proliferation Assays 3.1.1 Cells Preparation Peripheral blood mononuclear cells (PBMC) were separated from peripheral blood of donors known to be responders to Herpes Simplex Virus (HSV)-1, Rubella, and/or Tetanus toxoid. Whole blood was diluted 1:4 with HBSS, layered over Ficoll-Paque (Pharmacia LKB Biotechnology Inc., Piscataway, N.J.) and centrifuged at 1600 rpm for 30 minutes. PBMC were washed three times with HBSS, then cultured in medium containing RPMI 1640 supplemented with 5% human AB+ serum (Flow Labs, McLean, Va.), glutamine (2 mM), penicillin/streptomycin, sodium pyruvate and HEPES. For proliferation assays, cells were cultured in 96-well round-bottom microtiter plates in a humidified incubator with 5% CO$_2$ at 37° C. Jurkat cells were maintained in RPMI 1640 plus 10% FCS with supplements described above.

3.1.2 Proliferation Assays

To stimulate T cells with viral antigens, 10$^5$ PBMC/well were cultured with and without inhibitors with dilutions of concentrated culture fluids from HSV-1 or Rubella infected cells vs. control supernatant (SN) from uninfected cells (Microbix Biosystems Inc., Toronto, Ontario). SN contained virus inactivated by gamma radiation. HSV-1 cultures were pulsed with $^3$H-thymidine (TdR) on Day 3, and harvested on Day 4. Rubella cultures were pulsed on Day 5 and harvested on Day 6. PBMC from donors immunized against tetanus toxoid were cultured at 10$^5$/well for 5 days with dilutions of tetanus toxoid (0.4–4 LF/ml; Massachusetts Department of Public Health, Boston, Mass.).

Cells were pulsed overnight with 1 μCi/well of $^3$H-TdR (ICN, Irvine, Calif.) and harvested onto glass fiber filters using a PHD harvester (Cambridge Technology, Inc., Watertown, Mass.). Thymidine incorporation was measured by liquid scintillation counting using a Pharmacia Beta counter (Pharmacia LKB Nuclear, Inc., Gaithersburg, Md.).

Mitomycin-treated PBMC or stimulator cells were used in some experiments. Cells were suspended in HBSS at 10$^7$/ml and treated with 50 μg/ml of Mitomycin C (Sigma, St. Louis, Mo.) for 30 minutes at 37° C.

To measure T-cell responses to allo-antigens, PBLs were obtained from two MHC-disparate donors. One set of cells were treated with mitomycin c which then served as the stimulator cells. The other set was used as the responder cell population. The cells ($2\times10^5$ per well) were added to microculture wells and were pulsed 4–5 days later with tritiated thymidine as described above, harvested and radio-activity measured.

For the assay of CD8-bearing cells, a T cell line which was specific for Epstein Barr Virus (EBV)-transformed B cells was used. The line was generated from a normal human donor by repeated rounds of stimulation by EBV transformed B cells followed by expansion/rest periods in Interleukin 2 (IL-2). Greater than 80% of the T cells bear CD8 as judged by immunofluorescence. For these studies, the EBV line was treated with mitomycin c to prevent proliferation. T cells ($1\times10^5$) were added to microculture wells and proliferation measured as described above. Little to no cytotoxicity was observed by PIC 024.4 in this assay.

3.1.3 Effect on Antigen-dependent Proliferation of PBMCs

This assay was used to assess the effect of test compounds on the antigen-dependent proliferation of PBMCs. It serves as an indication of the extent to which the compounds affect normal T-cell function. Blood collected from normal, tetanus toxoid immunized donors was layered over Ficoll-Hypaque and centrifuged. Fractionated PBMCs were collected, washed three times with Hank's buffered saline solution (HBSS), and cultured in RPMI 1640 medium supplemented with 5% human AB+ serum, L-glutamine, penicillin/streptomycin, sodium pyruvate, and HEPES buffer. For the assay, cells were transferred to 96-well microtiter plates ($1\times10^5$ per well), treated with serial dilutions of PRO 2000 compound with or without tetanus toxoid (0.4–4 LF/ml), and incubated at 37° C. in a humidified 5% $CO_2$ atmosphere. On day 5, the cells were pulsed with [$^3$H]-thymidine (1 $\mu$Ci/well), incubated overnight, and harvested on glass-fiber filters.

Thymidine incorporation was measured by liquid scintillation counting.

Stimulation, as measured by [$^3$H]-thymidine incorporation, was unaffected by PIC 024.4 concentrations up to 50 $\mu$g/ml (FIG. 23). Interestingly, high concentrations of the compound caused unstimulated cells to undergo a low level of proliferation, but the effect was minimal. PIC 024.4 concentrations capable of suppressing HIV infection had no effect on tetanus toxoid-induced proliferation.

All of the 2000 fractions showed some inhibitory activity, but the $IC_{50}$'s were about two orders of magnitude higher than those observed in the syncytium inhibition assay (FIG. 24). The slight dependence on molecular weight was probably insignificant in this cell-based assay. None of the fractions affected unstimulated PBMC's.

3.1.4 Effect on Antigen-dependent Proliferation of a T-cell Clone

Murine L cells transfected with wild-type human HLA DR gene constructs ($10^6$/tube) were pulsed in Falcon $12\times75$ mm snap-cap polystyrene tubes with tissue culture medium or various doses of Influenza HA 307–319 peptide (0.03–1 $\mu$g/tube) in 0.4 ml of tissue culture medium for two hours at 37° C. in a humidified 5% $Co_2$ atmosphere. To block proliferation, L cells were treated with 100 $\mu$g/ml mitomycin C for the last hour of the incubation. The cells were then washed three times with tissue culture medium to remove residual peptide and mitomycin C. After the final wash, L cells were resuspended to $8\times10^5$ cells/ml. Influenza HA 307–319 peptide-specific HLA DR-restricted T cells ($3\times10^4$/well) were pre-incubated with serial dilutions of test compound for one hour at 37° C. in a humidified, 5% $CO_2$ atmosphere. T cells were then cultured with $4\times10^4$ mitomycin C-treated L cells in a final volume of 0.2 ml of tissue culture medium in round-bottomed 96-well microtiter plates. The cultures were incubated at 37° C. for a total of 3 days. Approximately 14 hours before termination of the culture, 0.5 $\mu$Ci of [$^3$H]-thymidine was added to each well. The cells were harvested using a cell harvester and [$^3$H]-thymidine was added to each well. The cells were harvested using a cell harvester and [$^3$H]-thymidine incorporation was determined by liquid scintillation counting.

3.1.5 Effect on Antigen-independent (IL-2-mediated) Proliferation of a T-cell Clone Influenza HA307–319 peptide-specific HLA DR-restricted T cells ($3\times10^4$/well) were pre-incubated with test compound for one hour at 37° C. in a humidified, 5% $CO_2$ atmosphere. T cells were then cultured with 10 units of recombinant human IL-2 in a final volume of 0.2 ml tissue culture medium in round-bottomed 96-well microtiter plates. The cultures were incubated at 37° C. for a total of 3 days. Approximately 14 hours before termination of the culture, 0.5 $\mu$Ci of [$^3$H]-thymidine was added to each well. The cells were harvested using a cell harvester and [$^3$H]-thymidine incorporation was determined by liquid scintillation counting, using a scintillation counter.

Results (3.1.4, 3.1.5)

PIC 024.4 was found to inhibit both antigen-dependent and antigen-independent proliferation of a T-cel clone, but only at concentrations significantly higher than those required to suppress HIV-1 infection (FIG. 25). The differential effects on viral infection and antigen-dependent T cell proliferation may be related to the fact that the region of CD4 required for MHC binding is distinct from the site required for gp120 binding. (Clayton et al., *Nature* 339:548–551 (1989)). Subsequent toxicology studies have shown that this class of compound has negligible effect on T-cell numbers or function in vivo.

3.2 Toxicity Testing

To determine whether PIC 024.4 had general antiproliferative effects (indicative of toxicity), they were tested with the various cell lines Jurkat (T leukemia), K562 (Erythroleukemia), U937 (histiocyte), CEM (T lymphoblast), and RS-EBV (EBV-transformed line). Cells ($5\times10^5$/ml) were incubated in microculture wells with various dilutions of PIC 024.4. Normally, the cells will proliferate spontaneously and this can be measured by evaluating $^3$H-thymidine uptake. After 24 hours, the cells were exposed to 1 $\mu$Ci of thymidine per well and 16 hours later the plates were harvested and filters counted for radioactivity. For comparison, standard wells were set up that received culture medium only and these wells served as the basis for determining inhibition of thymidine uptake. PIC 024.4 inhibited CEM cell proliferation by 14% at 100 $\mu$g/ml and RS-EBV cell proliferation by 27% at 100 $\mu$g/ml (30% polymer by weight).

Figure 1:
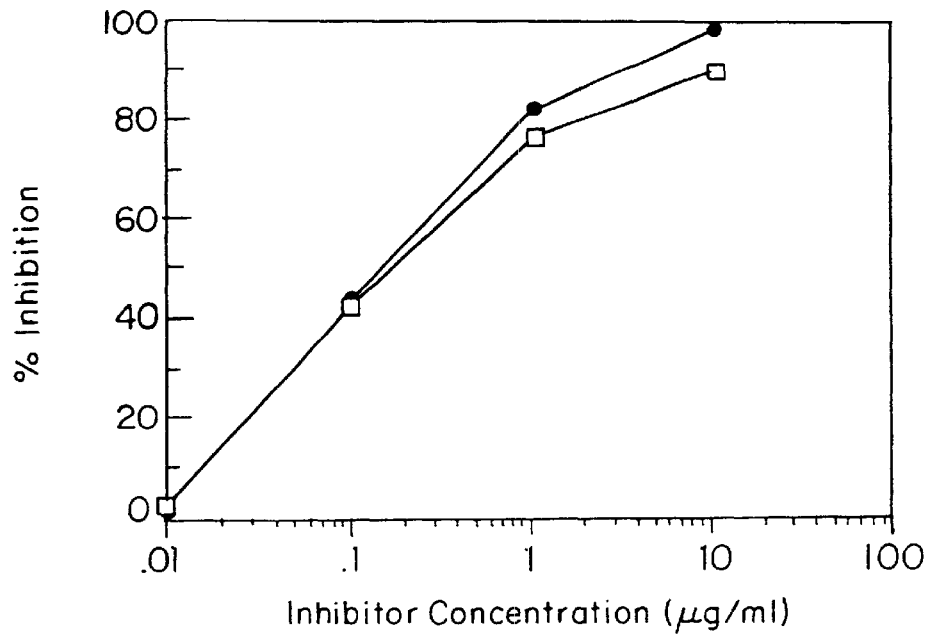
FIG. 1 is a graph of the inhibition of gp120 binding to immobilized soluble CD4 (sCD4) by PIC 024.4 (a formaldehyde/naphthalene sulfonic acid dispersant isolated from a Direct Yellow 29 composition, designated by an open square) and PRO 1041 (designated by a closed circle). Concentrations are based on total mass of material, (30% by wt. naphthalene sulfonic acid condensate (30% NSA)).

FIG. 1 illustrates the results of the CD4/gp120 ELISA assay with PIC 024.4 and PRO 1041. PIC 024.4 and PRO 1041 inhibit the binding of gp120 to CD4 in a dose-dependent manner with an $IC_{50}$ of about 0.2 $\mu$g/ml. The results of the Rosette Inhibition assay show no effect of PIC 024.4 on CD2/LFA-3 interactions at doses up to 100 $\mu$g/ml. The T cell proliferation assay shows a similar lack of effect at these doses. As shown by the in vitro toxicity testing, PIC 024.4 is not toxic at concentrations where it is active in inhibiting the CD4/gp120 interaction.

3.3 Anticoagulation Assay: Activated Partial 3.3.1 Thromboplastin Time Assay

Venous blood (9.0 ml) was added to 1 ml of 3.9% sodium citrate (ratio of 1:10) in a top vacutainer tube and immediately centrifuged. This step removed calcium, a required factor in coagulation. The specimen was free of hemolysis and clots.

A tube of 0.02 M calcium chloride solution was placed in the back of a Fibrometer heating block and allowed to reach about 37° C. Activated Cephaloplastin (0.1 ml, Dade) was mixed well and pipetted into three coagulation cups. The cups were warmed for about one minute at 37° C.

One ml of the above citrated plasma was incubated with the test compound for about 60 minutes at about 37° C. The incubated plasma (0.1 ml) was added to the first cup of cephaloplastin. At the end of the second minute, 0.1 ml of plasma was added to the second cup. At the end of the third minute, 0.1 ml of plasma was added to the third cup. After the addition of plasma to each cup, the contents were mixed well and incubated at about 37° C. for about 3 minutes each.

The octamer (PRO 1191) and hexamer (PRO 1073) showed no effect on APTT at 160 μg/ml (FIG. 27B).

The four PRO 2000 fractions were tested in the APTT assay. Anticoagulant activities were found to depend on molecular weight, with PRO 2000/25>PRO 2000/10>PRO 2000/5>PRO 2000/3 (FIG. 26). Concentrations producing an APTT of 70 seconds (double the upper limit of normal) were 40, 43, 135 and >160 μg/ml, respectively. The effect of PRO 2000/5 was ten-fold less severe than that of dextran sulfate. Note that for PRO 2000/5, the ratio of antiviral $IC_{50}$ (HIV-1 IIIB/CEM) to APTT doubling concentration is 1:68.

4. SUMMARY OF ACTIVITY 4.1 PIC 024.4

The results of the microbiological studies on PIC 024.4 are summarized in Table 9. Taken together, they establish that naphthalene sulfonic acid condensation polymers exhibit potent, selective antiviral activity by disrupting the HIV-1 infection process.

TABLE 9

Summary of the microbiological activity of PIC 024.4

| Assay | $IC_{50}$ (μg/ml)* |
|---|---|
| gp120/CD4 Binding Inhibition | 0.3 |
| CD2/CD58 Binding Inhibition | 71 |
| gp120/CEM Binding Inhibition | 3.5 |

TABLE 9-continued

Summary of the microbiological activity of PIC 024.4

| Assay | $IC_{50}$ (μg/ml)* |
|---|---|
| Antiviral Assays | |
| IIIB/CEM | 2.5 |
| JR-CSF/PBL | 1.5 |
| ADA/MO | 0.3 |
| IIIB/H9 | 0.5 |
| 14aPre | 10 |
| N70 | 4 |
| Ba-L | 1.2 |
| HL2/3 Syncytium Inhibition | 1.2 |
| Effect on T-cell Proliferation | |
| PBL (Ag-dependent) | >30 |
| Clone (Ag-dependent) | 9 |
| Clone (Ag-independent) | 21 |

Note: Italics indicate specificity controls
*based on 100% polymer by weight 4.2 Summary of the Activity of PRO 2000 Fractions Overall, the biological activities of the PRO 2000 fractions were comparable to those of crude PIC 024.4 (Table 10). Although the molecular weight dependence of these activities differed somewhat from assay to assay, the 5-, 10-, and 25-kD preparations generally showed similar potencies, while the 3-kD fraction was somewhat less potent. Importantly, PRO 2000/5 showed potent activity against a number of primary clinical isolates. The similar $IC_{50}$'s for inhibition of all of the isolates tested suggests that PRO 2000/5 blocks infection by binding to the CD4 receptor, and this is supported by the tight binding of the compound to the receptor. However, a mechanism involving interaction with the virus cannot be ruled out.

The activity of the 5-kD material was comparable to that of higher molecular weight fractions, and somewhat more potent than the smaller 3-kD material. Polyanions of about 5 kD have also been tested in humans. Furthermore, PRO 2000/5 displayed significantly less anticoagulant activity than PRO 2000/10 and PRO 2000/25 in an APTT assay. Overall, PRO 2000/5 appears to be the least toxic fraction that retains full biological activity.

TABLE 10

Biological activity of PRO 2000 fractions

| | $IC_{50}$ (μg/ml) | | | |
|---|---|---|---|---|
| Assay | PRO 2000/3 | PRO 2000/5 | PRO 2000/10 | PRO 2000/25 |
| gp120/CD4 Binding Inhibition | 1.1 | 0.36 | 0.15 | 0.12 |
| gp120/CEM Binding Inhibition | 4.9 | 1.9 | ≦1.4 | 1.6 |
| gp120/Whole Blood Inhibition | 151 | 35 | 17 | 11 |
| BIAcore Inhibition | 22 | 10 | 8 | 10 |
| MAb Binding Inhibition | | | | |
| Leu3A | >232 | >221 | 107 | 63 |
| 19Thy | >232 | 171 | 113 | 58 |
| OKT4 | >232 | >221 | >268 | >203 |
| Antiviral (IIIB/CEM) | 2.8 | 1.7 | 2.1 | 2.1 |
| | | 2.2 | | |
| Syncytium Inhibition | 0.4 | 0.6 | 0.7 | 0.7 |
| Effect on PBMC Proliferation | 60 | 40 | 24 | 24 |
| APTT (doubling of time | >160 | 135 | 43 | 40 |

4.3 Summary of the Activity of Defined Oligomers

Defined oligomers ranging in size from the dimer to the octamer were also able to block the gp120/CD4 interaction and inhibit HIV-1 infection in vitro (Table 11). Activities showed a strong dependence on size, with the octamer>hexamer≧tetramer>dimer. The octamer itself was less active than the higher-molecular-weight polymers (e.g. PRO 2000/5). Interestingly, the octamer and hexamer showed no effect on coagulation at concentrations up to 160 μg/ml. The ratio of antiviral $IC_{50}$ to APTT doubling concentration may therefore be quite favorable.

TABLE 11

Biological Activity of Oligomers

| Assay | $IC_{50}$ (μg/ml) | | | |
|---|---|---|---|---|
| | PRO 1191 | PRO 1073 | PRO 1072 | PRO 1055 |
| gp120/CD4 Binding Inhibition | 5 | 250 | >210 | 410 |
| gp120/CEM Binding Inhibition | 8 | 24 | 33 | 660 |
| gp120/Blood Binding Inhibition | 130 | 600 | N/A | N/A |
| IIIB/CEM Antiviral Assay | 25 | 28 | 78 | N/A |
| Syncytium Inhibition | 6 | 17 | 15 | 60 |
| Effect on PBMC Proliferation | >100 | >100 | N/A | N/A |
| APTT (doubling of clotting time) | >160 | >160 | N/A | N/A |

EQUIVALENTS

Those skilled in the art will recognize, or be able to ascertain, using no more than routine experimentation, many equivalents to the specific embodiments of the invention described specifically herein. Such equivalents are intended to be encompassed in the scope of the following claims:

We claim:

1. A narrow or mono-dispersed non-cyclic condensation polymer of a naphthalene sulfonic acid and formaldehyde or a pharmaceutically acceptable salt or prodrug thereof, wherein the peak molecular weight of said condensation polymer is sufficient to maintain anti-human immunodeficiency viral activity with a reduction in anti-coagulation as determined by an Activated Partial Thromboplastin Time assay.

2. The polymer of claim 1 wherein the therapeutic ratio is at least about 20.

3. The polymer of claim 1, wherein the narrow-dispersed polymer has a mean molecular weight of about 3 kDa±1 kDa.

4. The polymer of claim 1, wherein peak molecular weight is between about 0.7 kDa and about 4 kDa.

5. A narrow or mono-dispersed non-cyclic condensation polymer of a naphthalene sulfonic acid and formaldehyde or a pharmaceutically acceptable salt or prodrug thereof, wherein the peak molecular weight is between about 0.7 kDa and about 4 kDa.

6. A narrow or mono-dispersed non-cyclic condensation polymer of a naphthalene sulfonic acid and formaldehyde or a pharmaceutically acceptable salt or prodrug thereof, wherein the mean molecular weight is 3 kDa±1 kDa.

* * * * *